(12) United States Patent
Canifax et al.

(10) Patent No.: US 8,597,262 B2
(45) Date of Patent: Dec. 3, 2013

(54) APPARATUS AND METHODS OF TREATMENT OF PATHOLOGIC PROLIFERATIVE CONDITIONS UTERINE TISSUE

(75) Inventors: Rosa K. Canifax, Minnetonka, MN (US); Thomas Q. Dinh, Minnetonka, MN (US); Edouard A. Koullick, Minnetonka, MN (US); Mark S. Bouchier, Minnetonka, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 13/383,147

(22) PCT Filed: Aug. 16, 2010

(86) PCT No.: PCT/US2010/041525
§ 371 (c)(1),
(2), (4) Date: Feb. 29, 2012

(87) PCT Pub. No.: WO2011/006067
PCT Pub. Date: Jan. 13, 2011

(65) Prior Publication Data
US 2012/0150105 A1 Jun. 14, 2012

Related U.S. Application Data

(60) Provisional application No. 61/238,943, filed on Sep. 1, 2009.

(51) Int. Cl.
*A61M 31/00* (2006.01)
(52) U.S. Cl.
USPC .......................................................... 604/285
(58) Field of Classification Search
USPC .............................................. 604/285, 890.1
See application file for complete search history.

(56) References Cited

U.S. PATENT DOCUMENTS 3,896,819 A * 7/1975 Zaffaroni et al. .............. 128/833
3,993,057 A * 11/1976 Ramwell ....................... 128/833

(Continued)

FOREIGN PATENT DOCUMENTS

EP 0 778 004 3/2003
WO WO 00/33724 6/2000

(Continued)

OTHER PUBLICATIONS

Harmanli, Ozgur H., et al., "Transvaginal Uterine Artery Ligation in a Woman with Uterine Leiomyomas—A Case Report," The Journal of Reproductive Medicine, p. 384.

(Continued)

*Primary Examiner* — Aarti B Berdichevsky
(74) *Attorney, Agent, or Firm* — Kagan Binder, PLLC

(57) ABSTRACT

A uterine fibroid treatment device providing for localized delivery of one or more treatment drugs for treating various uterine conditions including, for example, uterine fibroids, abnormal uterine bleeding, pelvic adhesions and endometriosis. Generally, the uterine treatment device comprises a physical positioning element that can be inserted, positioned and maintained in close proximity to the uterine tissue to be treated. The treatment drugs delivered to the treatment location can include various combinations of anti-proliferative agents and angiogenesis inhibitors to provide different treatments concurrently. In some embodiments, the physical element can also serve the dual purpose of delivering the treatment drugs while simultaneously cutting off blood flow to a mature fibroid to initiate hypoxic/ischemic conditions within the mature fibroid.

17 Claims, 37 Drawing Sheets

(56) References Cited

U.S. PATENT DOCUMENTS

| | | | |
|---|---|---|---|
| 4,292,965 A * | 10/1981 | Nash et al. | 128/833 |
| 4,341,728 A * | 7/1982 | Robertson et al. | 264/161 |
| 4,596,249 A | 6/1986 | Freda et al. | |
| 4,612,924 A * | 9/1986 | Cimber | 128/836 |
| 4,957,498 A | 9/1990 | Caspari et al. | |
| 5,059,201 A | 10/1991 | Asnis | |
| 5,188,636 A | 2/1993 | Fedotov | |
| 5,290,303 A | 3/1994 | Pingleton et al. | |
| 5,364,408 A | 11/1994 | Gordon | |
| 5,431,666 A | 7/1995 | Sauer et al. | |
| 5,488,958 A | 2/1996 | Topel et al. | |
| 5,522,820 A | 6/1996 | Caspari et al. | |
| 5,544,664 A | 8/1996 | Benderev et al. | |
| 5,562,686 A | 10/1996 | Sauer et al. | |
| 5,613,974 A | 3/1997 | Andreas et al. | |
| 5,645,552 A | 7/1997 | Sherts | |
| 5,728,112 A | 3/1998 | Yoon | |
| 5,766,183 A | 6/1998 | Sauer | |
| 5,797,927 A | 8/1998 | Yoon | |
| 5,843,126 A | 12/1998 | Jameel | |
| 5,863,294 A | 1/1999 | Alden | |
| 5,935,149 A | 8/1999 | Ek | |
| 5,979,453 A | 11/1999 | Savage et al. | |
| 6,032,673 A | 3/2000 | Savage et al. | |
| 6,059,766 A | 5/2000 | Greff | |
| 6,254,601 B1 | 7/2001 | Burbank et al. | |
| 6,468,228 B1 | 10/2002 | Topel et al. | |
| 6,500,168 B1 * | 12/2002 | Jellie | 604/890.1 |
| 6,546,933 B1 | 4/2003 | Yoon | |
| 6,550,482 B1 | 4/2003 | Burbank et al. | |
| 6,551,331 B2 | 4/2003 | Nobles et al. | |
| 6,602,251 B2 | 8/2003 | Burbank et al. | |
| 6,635,065 B2 | 10/2003 | Burbank et al. | |
| 6,638,286 B1 | 10/2003 | Burbank et al. | |
| 6,746,456 B2 | 6/2004 | Xiao | |
| 6,780,168 B2 * | 8/2004 | Jellie | 604/107 |
| 6,955,643 B2 | 10/2005 | Gellman et al. | |
| 7,033,370 B2 | 4/2006 | Gordon et al. | |
| 7,060,077 B2 | 6/2006 | Gordon et al. | |
| 7,713,573 B2 * | 5/2010 | Owens et al. | 427/2.1 |
| 2002/0124853 A1 | 9/2002 | Burbank et al. | |
| 2002/0165579 A1 | 11/2002 | Burbank et al. | |
| 2002/0183771 A1 | 12/2002 | Burbank et al. | |
| 2003/0120286 A1 | 6/2003 | Burbank et al. | |
| 2003/0120306 A1 | 6/2003 | Burbank et al. | |
| 2003/0191391 A1 | 10/2003 | Burbank et al. | |
| 2004/0092979 A1 | 5/2004 | Burbank et al. | |
| 2004/0097961 A1 | 5/2004 | Burbank et al. | |
| 2004/0097962 A1 | 5/2004 | Burbank et al. | |
| 2004/0153105 A1 | 8/2004 | Burbank et al. | |
| 2004/0158262 A1 | 8/2004 | Burbank et al. | |
| 2004/0202694 A1 | 10/2004 | Burbank et al. | |
| 2005/0245947 A1 | 11/2005 | Harmanli | |
| 2006/0193887 A1 * | 8/2006 | Owens et al. | 424/423 |
| 2010/0166826 A1 * | 7/2010 | Kiser et al. | 424/426 |
| 2011/0017219 A1 * | 1/2011 | de Graaff et al. | 128/833 |
| 2011/0208118 A1 * | 8/2011 | Katz | 604/57 |
| 2011/0271963 A1 * | 11/2011 | Bar-Am | 128/833 |
| 2012/0271230 A1 * | 10/2012 | Arnal et al. | 604/93.01 |

FOREIGN PATENT DOCUMENTS

| | | | | |
|---|---|---|---|---|
| WO | WO 2005/112789 | | 12/2005 | |
| WO | WO 2009073782 A2 * | | 6/2009 | A61K 31/4745 |

OTHER PUBLICATIONS

"Uterine Artery Occlusion by Embolization or Surgery for the Treatment of Fibroids: A Unifying Hypothesis—Transient Uterine Ischemia," The American Association of Gynecologic Laparascopists, vol. 7 No. 4, pp. S1-S49, Nov. 2000.

Chordia, S.K.S., "Management of a bleeding aberrant cervical artery following vacuum suction termination. Case report," British Journal of Obstetrics and Gynaecology, vol. 95, pp. 411-413, Apr. 1988.

Lichtinger et al., "Temporary, transvaginal occlusion of the uterine arteries: A feasibility and safety study," Journal of Minimally Invasive Gynecology 12, pp. 40-42, 2005.

Mitchell et al., "Pregnancy Following Bilateral Uterine Artery Ligation," British Journal of Obstetrics and Gynaecology, vol. 84, pp. 551-554, Jul. 1977.

Mullins et al., "Uterine Artery Ligation for Postabortal Hemmorhage," Am J. Obst. & Gyne., vol. 54, No. 3, pp. 383-384, Sep. 1979.

\* cited by examiner

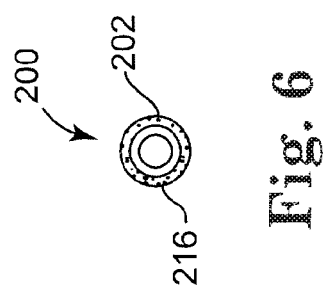
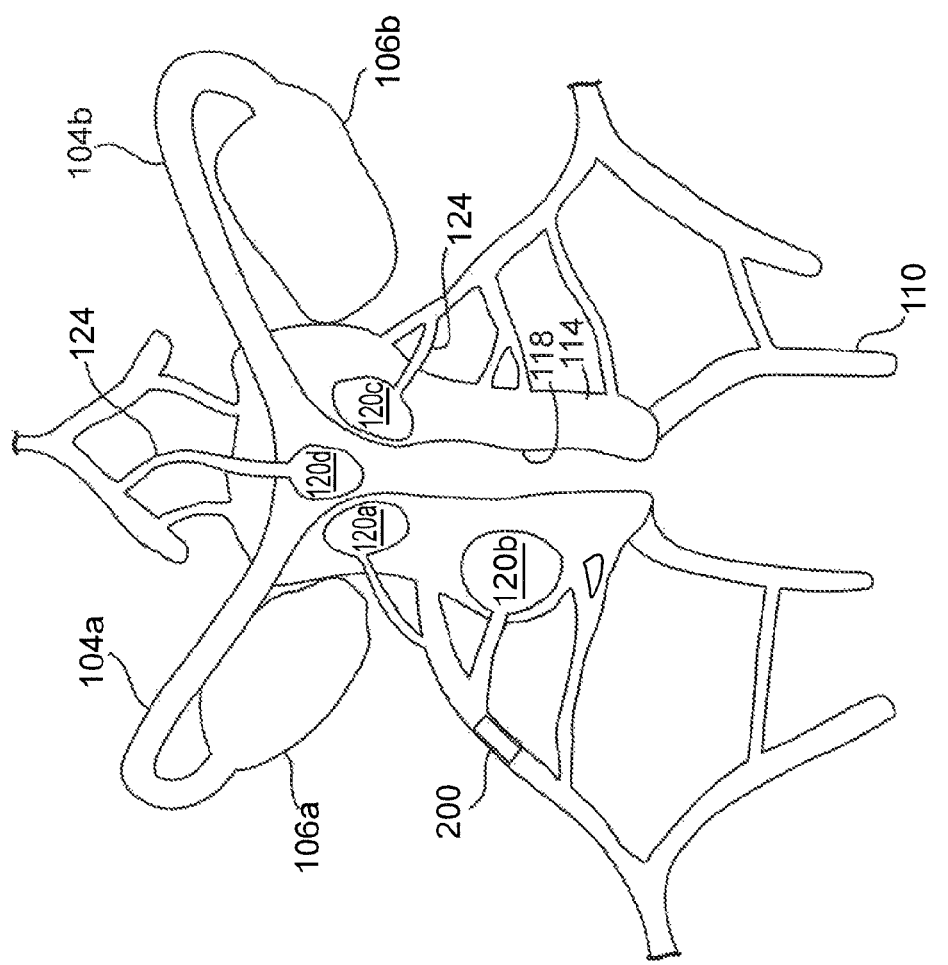

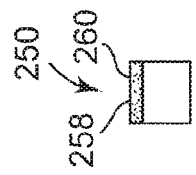
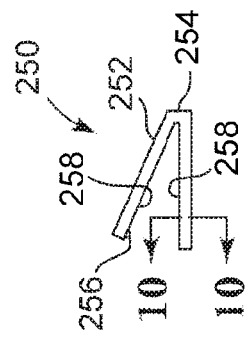
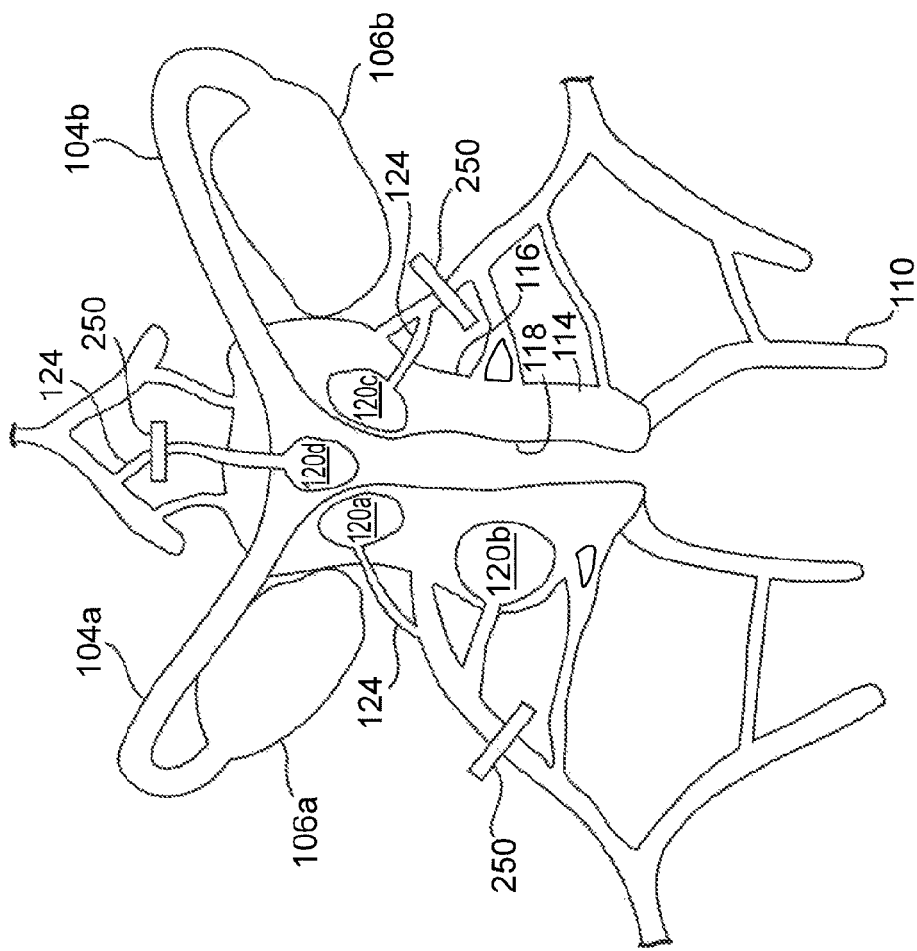

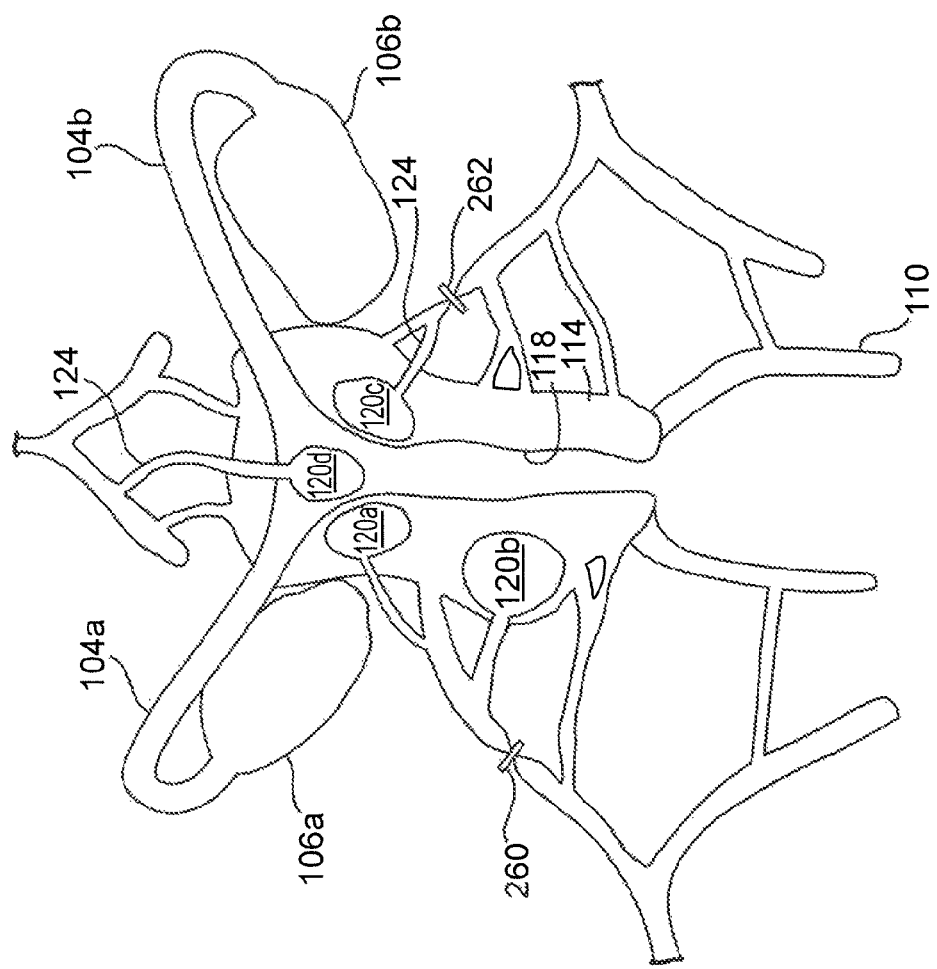

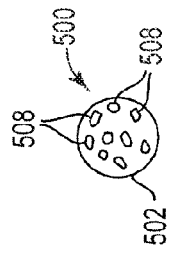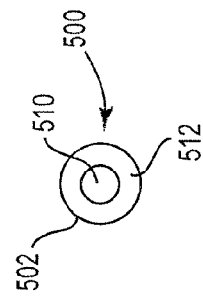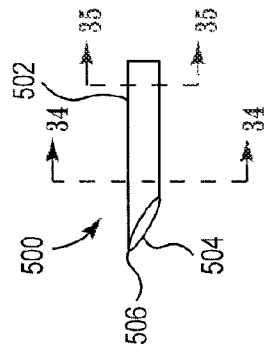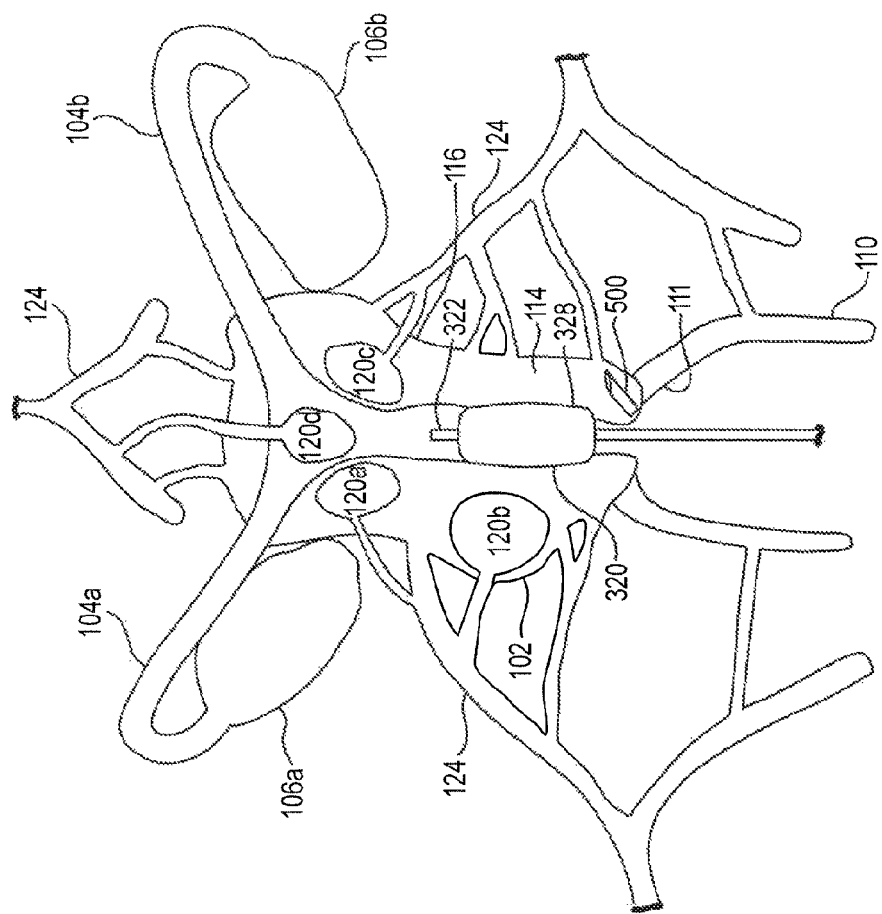

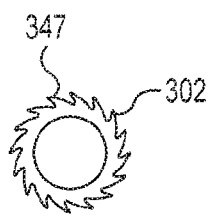
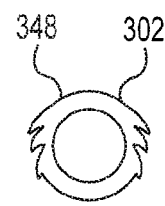
Fig. 62     Fig. 63
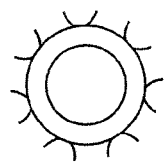
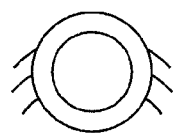
Fig. 64     Fig. 65
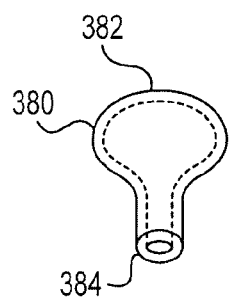
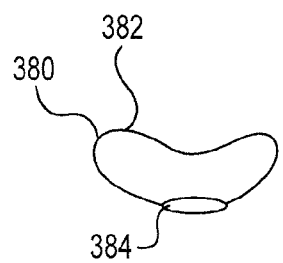
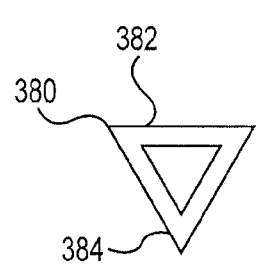
Fig. 66     Fig. 67     Fig. 68

APPARATUS AND METHODS OF TREATMENT OF PATHOLOGIC PROLIFERATIVE CONDITIONS UTERINE TISSUE

This application claims the benefit from International No. PCT/US2010/041525, which was granted an International Filing Date of Aug. 16, 2010, which in turn claims priority to U.S. Provisional Application Ser. No. 61/238,943, filed Sep. 1, 2009 and entitled "INTRAVAGINAL TREATMENT OF UTERINE FIBROIDS," which is herein incorporated by reference in its entirety.

PRIORITY CLAIM

The present application claims priority to U.S. Provisional Application Ser. Nos. 61/244,385, filed Jul. 9, 2009 and entitled "INTRAVAGINAL TREATMENT OF UTERINE FIBROIDS", and 61/238,943, filed Sep. 1, 2009 and entitled "INTRAVAGINAL TREATMENT OF UTERINE FIBROIDS," each of which are herein incorporated by reference in their entirety.

FIELD OF THE DISCLOSURE

The present disclosure relates generally to treatment of uterine conditions resulting from cellular proliferation. More specifically, the present disclosure relates to a device for localized delivery of various treatment drugs for treatment of uterine fibroids so as to maintain systemic levels of the drug that are commonly associated with certain side effects, including immuno suppression.

BACKGROUND OF THE DISCLOSURE

A variety of pathological conditions of the uterus are the result of cellular proliferation or abnormal cell division and growth of the myometrium or endometrium. Representative uterine conditions can include fibroids, abnormal uterine bleeding, pelvic adhesions, endometriosis and the like.

Uterine leiomyomas or fibroids are the most common tumor of the female reproductive tract affecting 20-25% of all women during their reproductive years. While uterine fibroids are generally non-cancerous, their presence can lead to a variety of problems including excessive uterine bleeding, pain and even infertility. Because of these possible issues, a variety of treatment options have been developed to address the presence of uterine fibroids.

One common method, and the most drastic, for eliminating uterine fibroids is the surgical removal of the uterus or hysterectomy. Generally, hysterectomies are performed on women who are beyond their child bearing years or have made the decision to forego bearing children. A hysterectomy is an invasive surgical procedure in which the uterus must be sufficiently exposed such that the attached vascular network, fallopian tubes and ligaments can be severed. In addition to eliminating a woman's ability to bear children, a hysterectomy as a truly invasive surgery has the potential for a variety of surgical consequences including complications such as, for example, blood loss, pain and discomfort, extended convalescence and potentially increased costs due to extended and further hospital care.

Uterine fibroids can form in a variety of locations along the uterus with each location providing a unique set of symptoms and effecting surrounding tissue in different ways. Regardless of location, uterine fibroids rely on the highly vascularized nature of the female reproductive system to grow and develop. As such, a variety of alternative treatment methods have been proposed in which the blood vessels connected to said uterine fibroids are accessed to provide treatment. For example, U.S. Pat. No. 6,059,766 proposes accessing vessels of the fibroid mass such that a minimally invasive catheter or probe can administer an embolyzing material. Another alternative treatment method has proposed temporary clamping of the vessels supplying a fibroid mass for a period long enough to cause fibroid cell death without permanently reducing blood flow to the myometrium and ovaries while also avoiding ischemia injury.

Finally, a variety of treatment protocols have been proposed in which the physical structure of the uterine fibroid is attacked so as result in tissue ablation and in some instances, physical removal of only the fibroid mass. For example, it has been proposed that appropriate medical imaging technologies can be utilized to deliver high intensity focused ultrasound (HIFU) energy into the fibroid mass to ablate the tissue wherein the fibroid can be resorbed within the body. In other instances, it has been proposed to introduce a cryogenic instrument capable of freezing, and thereby, killing the fibroid cells. Finally, a variety of minimally invasive instruments have been proposed to core or debulk fibroid masses wherein the material can then be removed by a suction device.

While a variety of procedures have been contemplated for treatment of uterine fibroids, there remains a need for new minimally invasive procedures that delivery effective treatment options while reducing the potential for negative treatment outcomes.

SUMMARY OF THE DISCLOSURE

The present application describes a uterine fibroid treatment device that provides for localized delivery of one or more treatment drugs for treating various uterine conditions including, for example, uterine fibroids, abnormal uterine bleeding, pelvic adhesions and endometriosis. Generally, the uterine treatment device comprises a physical positioning element that can be inserted, positioned and maintained in close proximity to the uterine tissue to be treated. Depending upon tissue location and the desired treatment regimen, the physical element can take on a variety of physical configuration including, for example, an occluding stent, a vaginal ring, an inflation balloon, a constricting band, clamp or suture, microspheres, gel, IUD, spring or pipe cleaner-like configurations, sponges, discs, silicone plugs/members, slings, prolapse mesh and the like. Generally, the treatment drugs delivered to the treatment location by the physical element includes one or more anti-proliferative agents that are absorbed, encapsulated or integrated with the physical element. Representative anti-proliferative agents can include, for example, rapamycin, rapamycin analogs, podophyllotoxin, podophyllotoxin analogs, curcumin, halofuginone and 2-methoxyestradiol. By delivering the one or more anti-proliferative drugs locally as opposed to systemically such as by, for example, intravenous or oral administration, dosage levels of the anti-proliferative agent can be delivered at lower levels so as to avoid or at least minimize common side effects such as, for example, immunodeficiency issues and potential toxic consequences. The treatment drugs can also alternatively comprise one or more angiogenesis inhibitors that are absorbed, encapsulated or integrated with the physical element. The treatment drugs delivered to the treatment location can also comprise various combinations of anti-proliferative agent(s) and angiogenesis inhibitor(s) to provide different treatments concurrently. In some embodiments, the physical element can also serve the dual purpose of delivering the treatment drug(s) while simultaneously cutting off blood flow to a mature fibroid to initiate hypoxic/ischemic conditions within the mature fibroid. In this dual capacity, the physical element and treatment drugs can inhibit the formation of a vascular network within the fibroid, prevent the revival of mature proliferative cells and/or prevent further growth and development of non-mature proliferative cells. After a period time, the lack of oxygen kills mature cells and can induce proliferation within non-mature cells. At this point, the treatment drugs can prevent non-mature cells from maturing.

In one aspect of the present disclosure, a device for the treatment of pelvic proliferative conditions comprises a physical member for local delivery of treatment drugs such as anti-proliferative agents or angiogenesis inhibitors. In one embodiment, the device provides for the treatment of uterine proliferative conditions by utilizing the physical member to locally deliver one or more treatment drugs to uterine proliferative cells including, for example, uterine fibroids. Alternatively, male pelvic tissue including prostate or testes tissue having proliferative conditions can be similarly treated with the device. Representative physical members are generally configured to maintain their position proximate tissue to be treated and can include, for example, an occluding stent, a vaginal ring, an inflation balloon, a constricting band, clamp or suture, micro spheres, gel, IUD, spring or pipe cleaner-like configurations, sponges, discs, silicone plugs/members, slings, prolapse mesh and the like. The treatment drug(s) are delivered with the physical member by coating the physical member, encapsulating the treatment drug(s) within the physical member or otherwise integrating the treatment drug(s) into the physical member. Representative Anti-proliferative agents can include, for example, rapamycin, rapamycin analogs, podophyllotoxin, podophyllotoxin analogs, curcumin, halofuginone and 2-methoxyestradio. As the treatment drug(s) are delivered locally, the treatment drug(s) can be delivered at dosage levels lower than typically necessary for treatment of mature proliferative cells such that immunodeficiency issues and potential toxic consequences often associated with anti-proliferative agents and angiogenesis inhibitors can be at least minimized if not eliminated entirely. In some embodiments, the physical member can perform the additional function of blocking the flow of blood and consequently oxygen to mature proliferative cells to initiate hypoxic and ischemic conditions within the uterine fibroids and to further assist in eliminating and/or preventing growth of uterine fibroids. In some embodiments, the device can further include additional therapeutic agents such as, for example, pain relieving medication, so as to alleviate discomfort associated with treatment of the proliferative condition.

In another aspect of the present disclosure, a device can be delivered intravaginally to deliver treatment drugs for the treatment of female proliferative conditions, such as anti-proliferative agents, angiogenesis inhibitors or combinations thereof. The minimally invasive device can comprise a physical structure impregnated with, molded with, coated with or otherwise retaining the one or more treatment drugs. The minimally invasive device generally comprises a physical device capable of maintaining its position proximate the tissue to be treated. Specifically, the minimally invasive device can comprise tabs of various sizes and shapes for gripping the tissue walls proximate the treatment location to maintain position of the minimally invasive device after implantation. Similarly, the minimally invasive device can alternatively or additionally comprise surface texturing to further grip the tissue walls proximate the treatment location to maintain the position of the device. In another aspect of the present disclosure, the device can comprise a corkscrew shape for burrowing a portion of the device into the tissue wall proximate to the treatment location to maintain the position of the minimally invasive device.

In another aspect of the present disclosure, a uterine treatment system can comprise an occlusion device including a treatment drug for positioning in a lumen proximate uterine tissue to be treated or alternatively, within a vascular network supplying proliferative cells. The occlusion device can comprise an occluding stent that is delivered into a suitable lumen such as, for example, a patient's fallopian tubes or uterine artery utilizing a conventional balloon catheter. The occluding stent can be crimped in place over the balloon catheter such that upon inflation of the balloon, the occluding stent is expanded so as to be retained in place within the lumen. The occluding stent can be coated and/or molded with one or more treatment drugs, such as anti-proliferative agents, angiogenesis inhibitors or combinations thereof. Representative antiproliferative agents can include rapamycin, rapamycin analogs, podophyllotoxin, podophyllotoxin analogs, curcumin, halofuginone and 2-methoxyestradiol. Through local delivery of the treatment drugs to the uterine tissue to be treated, the dosage levels of the treatment drugs can be reduced as compared to conventional systemic delivery vehicles such that potential damaging and/or toxic side-effects associated with the use of treatment drugs such anti-proliferative agents or angiogenesis inhibitors, can be reduced if not eliminated entirely. In some embodiments, the occluding stent can further induce hypoxic/ischemic conditions within proliferative cells to further assist in treating uterine tissue.

In another aspect of the present disclosure, a method for treating uterine proliferative conditions can comprise administering locally one or more treatment drugs to treat uterine fibroids. Generally, local administration of treatment drugs such anti-proliferative agents or angiogenesis inhibitors, includes positioning a physical member proximate the uterine tissue to be treated. The administration of the one or more anti-proliferative agents can be accomplished by incorporating the one or more anti-proliferative agents into the physical device. Suitable methods can be utilized to incorporate the anti-proliferative agent into the physical device including, for example, coating, encapsulating or otherwise integrating the anti-proliferative agent into the physical device. In some embodiments, the physical member can comprise an occlusive member introduced directly into a lumen proximate the uterine fibroids. In some other embodiments, the physical member can comprise a vaginally introduced member. In some preferred embodiments, administering the anti-proliferative agent can comprise administering reduced dosage levels of anti-proliferative agents and/or angiogenesis inhibitors than would be typically necessary for systemic delivery, including oral or intravenous delivery of the treatment drugst. In some embodiments, the method can further comprise inducing ischemic/hypoxic conditions within mature proliferative cells by blocking blood and consequently oxygen flow to the proliferative cells with the physical member.

In another aspect of the present disclosure, a system and related method for treating proliferative conditions can comprise an implantable physical member adapted to degrade or be absorbed by the body after implantation to gradually release the treatment drugs over a period of time. The implantable physical member can comprise gel inserts, polymer inserts or polymer rods. The system can also comprise positioning locally a plurality of microspheres formulated to gradually disperse one or more treatment drugs over a period of time. The microspheres can encapsulate one or more treatment drugs including one or more anti-proliferative agents, one or more angiogenesis inhibitors or combinations thereof to customize the type treatment to developmental state of the fibroid. Nanospheres encapsulating a treatment drug or a combination of treatment drugs can be packed within the microspheres to delay release of the treatment drug(s) until the treatment drugs are fully dispersed through the treatment area within the nanospheres.

The above summary of the invention is not intended to describe each illustrated embodiment or every implementation of the present invention. The figures and the detailed description that follow more particularly exemplify these embodiments.

BRIEF DESCRIPTION OF THE FIGURES

These as well as other objects and advantages of this invention, will be more completely understood and appreciated by referring to the following more detailed description of the presently preferred exemplary embodiments of the invention in conjunction with the accompanying drawings of which:

FIG. 6 is as section view of the expandable occlusion stent of FIG. 3 taken at line 6-6 of FIG. 5.

FIG. 7 is an illustration of an embodiment of a physical device for treatment of uterine proliferative conditions.

FIG. 8 is an illustration of an embodiment of a physical device for treatment of uterine proliferative conditions.

FIG. 9 is a plan view of a clip for treatment of uterine proliferative conditions.

FIG. 10 is a section view of the clip of FIG. 9 taken at line 10-10 of FIG. 9.

FIG. 11 is an illustration of embodiments of a physical device for treatment of uterine proliferative conditions.

FIG. 32 is an illustration of a female reproductive system including a vaginally introduced device for treatment of proliferative cellular conditions.

FIG. 33 is a plan view of an insertion rod for treatment of uterine fibroids.

FIG. 34 is a section view of the insertion rod of FIG. 33 taken at line 34-34 of FIG. 33 according to an embodiment of the invention.

FIG. 35 is a section view of the insertion rod of FIG. 33 taken at line 35-35 of FIG. 33 according to an embodiment of the invention.

FIG. 39 is a chart illustrating fibroid drug screening results for Eker rat leiomyoma (ELT3) cell line cells with Curcumin, Tranilast, Halofuginone, 2-methoxyestradiol and Sulfasalazine at various concentration levels.

FIG. 62 is a side view of a drug eluting intravaginal ring having a plurality of shaped ridges according to an embodiment of the invention.

FIG. 63 is a side view of a drug eluting intravaginal ring having a plurality of shaped ridges according to an embodiment of the invention.

FIG. 64 is a side view of a drug eluting intravaginal ring having a plurality of approximating elements according to an embodiment of the invention.

FIG. 65 is a side view of a drug eluting intravaginal ring having a plurality of approximating elements according to an embodiment of the invention.

FIG. 66 is a side view of a vaginally introduced device countered fit the shape of the vaginal cavity according to an embodiment of the invention.

FIG. 67 is a side view of a vaginally introduced device countered fit the shape of the vaginal cavity according to an embodiment of the invention.

FIG. 68 is a side view of a vaginally introduced device countered fit the shape of the vaginal cavity according to an embodiment of the invention.

Figure 1:
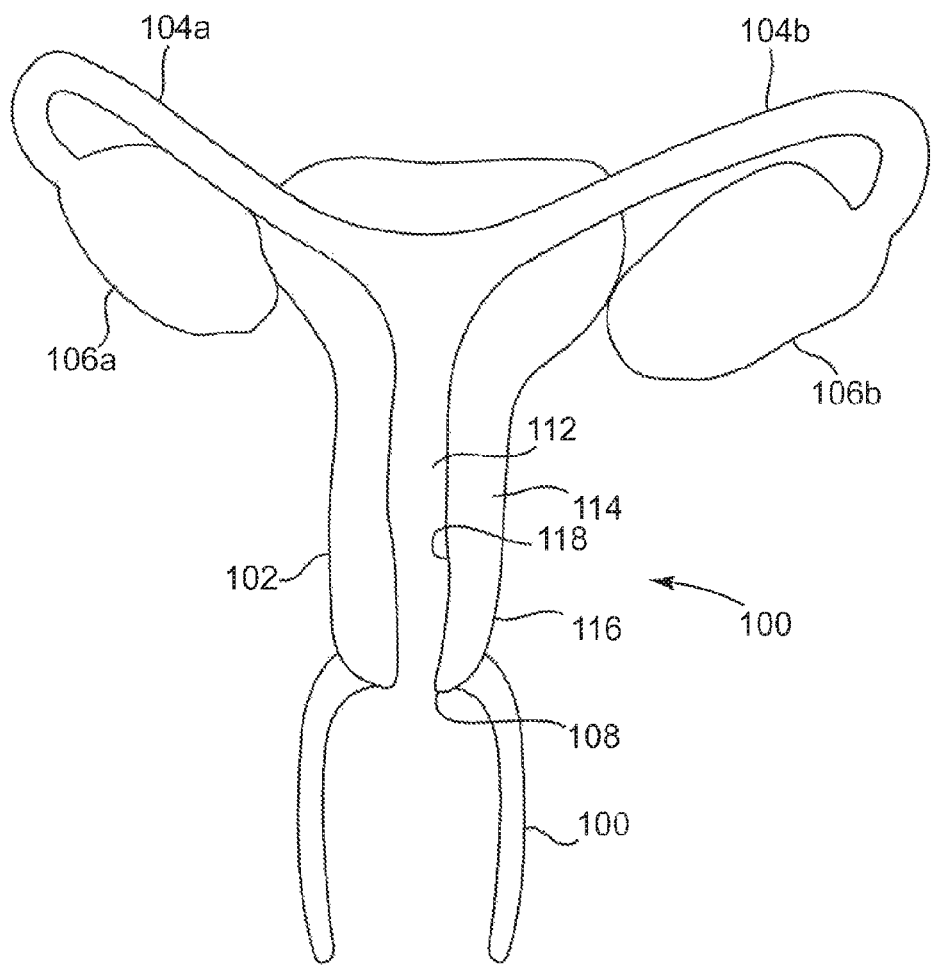
FIG. 1 is an illustration of a female reproductive system.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE DISCLOSURE

The present disclosure is directed to a device for the treatment of pelvic proliferative conditions. As described throughout the following detailed description, the device can provide for treatment of female pelvic proliferative conditions including, for example, uterine fibroids, abnormal uterine bleeding, pelvic adhesions, endometriosis and the like. It is to be understood that various described embodiments will find similar application with male pelvic proliferative conditions including, for example, proliferative cells located within prostate or testes tissue.

Figure 2:
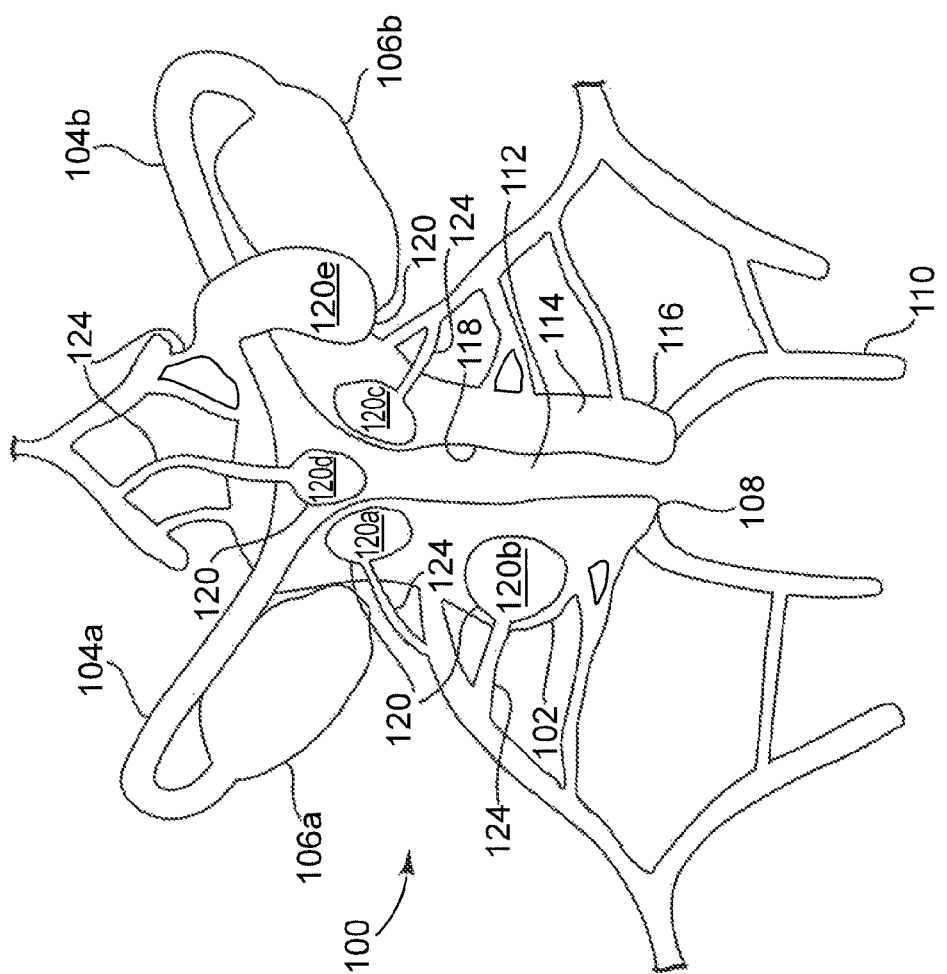
FIG. 2 is an illustration of a female reproductive system including a plurality of uterine fibroids.

As illustrated generally in FIG. 1, a female reproductive tract 100 generally comprises uterus 102, fallopian tubes 104a, 104b, ovaries 106a, 106b, cervix 108 and vagina 110. The uterus 102 defines a uterine cavity 112 connecting the vagina 110 with fallopian tubes 104a, 104b, thus allowing for the passage and fertilization of female reproductive cells. The uterus 102
is generally defined by a uterine wall 114 having an outer membrane or myometrium 116 and an inner membrane or endometrium 118. Referring to FIG. 2, female reproductive tract 100 is again illustrated with the further inclusion of mature proliferative cells, herein depicted as a plurality of uterine fibroids 120. Generally uterine fibroids 120 are distinguished relative to their positioning with respect to the uterine wall 114. For example, uterine fibroid 120a is generally referred to an intramural uterine fibroid and is positioned within the myometrium 116 which can distort the contour of uterine cavity 112. Uterine fibroid 120b is referred to as a subserosal uterine fibroid and is positioned just under the uterine serosa and may be attached to the corpus. Uterine fibroid 120c is referred to as a submucosal uterine fibroid and is located within the myometrium 116 and proximate the endometrium 118 thereby causing the endometrium 118 to bulge into uterine cavity 112. Uterine fibroids 120d and 120e are referred to as pedunculated uterine fibroids with uterine fibroid 120d extending into the uterine cavity 112 while uterine fibroid 120e extends into available space outside the myometrium 116. Uterine fibroids 120 generally comprise well circumscribed, solid and typically benign fibroid masses composed of smooth muscle cells and collagen. Uterine fibroids 120 receive nourislunent through a discrete vascular network 124 including veins and arteries that extends from myometrium 116.

According to the present invention, treatment of mature proliferative cells, i.e., uterine fibroids 120, is accomplished through local delivery of one or more treatment drugs to prevent further growth and even shrink the size of uterine fibroids 120 as opposed to physical removal of uterine fibroids 120. The treatment drugs can include one or more anti-proliferative agents, one or more autogenesis inhibitors or combinations thereof. In order to deliver the treatment drugs locally, a physical device is fabricated capable of remaining positioned proximate the uterine fibroids 120 that are to be targeted. The physical device includes the treatment drugs for administration over an extended period of time so as to prevent further growth and shrink the uterine fibroids 120. Generally, the treatment drug or drugs are coated, encapsulated or otherwise integrated with the physical device. By targeting uterine fibroids 120 with localized delivery of the treatment drugs, dosage levels conventionally associated with systemic delivery methods such as, for example, oral or intravenous introduction, can be substantially reduced to reduce or otherwise eliminate potential side effects and toxic consequences commonly experienced with the use of treatment drugs such as anti-proliferative agents or autogenesis inhibitors. In some embodiments, the physical device can provide the dual function of targeting and limiting blood supply and consequently, oxygen to uterine fibroids 120 so as to induce hypoxic/ischemic conditions within the uterine fibroids 120. By reducing or eliminating oxygen to the uterine fibroids 120, the mature proliferative cells are effectively killed and recurrence of uterine fibroids 120 is prevented.

In one representative embodiment, the treatment drug comprises an anti-proliferative agent having one or more of rapamycin or rapamycin analogs. Additionally, representative anti-proliferative agents can include, for purposes of example, 2-methoxyestradiol, 13-cis retinoic acid, 5-FU (fluorouracil), 9-cis retinoic acid, aclarubicin, all-trans retinoic acid, amcinomide, amsacrine, antisense c-myc, ascomycin, azathioprine, baxiliximab, beclomethasone betalapachone. betamethasone betamethasone, Betulinic acid and bexarotene, bleomycin, busultan, busultan, camptotecin and its derivatives, camptothecin, capecitabine, carboplatin, carmustine, celecoxib, chlomethine, chlorambucil, chlorambucil, chloromethane, cisplatin, cladribine, clobetasol propionate, crisataspase, curcumin, cycloepoxydon tepoxalin, cyclophosphamide, cyclophosphamide, cyclosporine, cytrarbine, dacarbazine, daclizumab, daunorubicin, dexamethasone, diacetate, diclofenal, diflorsasone, dipropionate, dipropionate, docetaxel, doxorubicin, epirubicin, epothilone A, epothilone B, epothilone D, estramustine, etanercept, etodolac, fludarabine, fluocinomide, gemtabine, gliotoxin G, halobetasol propionate, halofuginone, hydroxychloroquine, hydroxylcarbamide, ifosfamide, ifosfamide, indomethacin, Infliximab, interferon alpha, interferon beta, Leflunomide, lomustine, lomustine, maytasine, meclofenate, mefenamic acid, meloxicam, mephalan, mephalan, mercaptopurine, methotrexate, minocycline, mithramycin, mitobronitol, mitoxantrone, mycophenolic acid, nambunetone, oxiplatin, paclitaxel, panepoxydone, penicillamine, pentostatin, phenylbutazone, pioglitazone, piroxicam, podophyllotoxin analogs, podophyllotoxin, procarbazine, proteasome inhibitors, rosiglitazone, S-nitrosoglutathione, sulfalazine, sulinadac, tacrolimus, thiotepa, tioguanine, treosulfan, triamcinolone acetonide, troglitazone, valdecoxib, valerate, vinblastine, vincristine, vindesine, vinorelbine, β-estradiol, Used individually or in combination, these anti-proliferative agents generally function to prevent the proliferation of smooth muscle cells and can shrink mature fibroids by killing mature smooth muscle cells. In addition to preventing proliferation of smooth muscle cells, these anti-proliferative agents can provide additional beneficial mechanisms such as, for example, acting in an anti-inflammatory or anti-angiogenic capacity. In addition, anti-fibrosis agents such as Tranilast and halofuginone can be used in combination with other anti-proliferative agents since uterine fibroids also consist of collagen.

In one representative embodiment, the treatment drug comprises an angiogenesis inhibitor for inhibiting the formation of a vascular network in the fibroid. When combined with anti-proliferative agents, the treatment drugs comprising angiogenesis inhibitor and anti-proliferative agents so as to simultaneously starve mature fibroids and prevent the formation of new fibroids. Representative angiogenesis inhibitors include, for purposes of example, Batimastat; Marimastat; AG3340; Neovastat; PEX; TIMP-1, -2, -3, -4; PAI-1, -2; uPA Ab, uPAR Ab, Amloride, Minocycline, tetracyclines, steroids, cartilage-derived TIMP, αvβ3 Ab, Vitaxin, RGD containing peptides, αvβ5 Abm, Benzodiazepine derivatives, Endostatin, Angiostatin, asAT, IFN-α, IFN-γ, IL-12, nitric oxide synthese inhibitors, TSP-1, TNP-470, Combretastatin A4, Thalidomide, Linomide, PF-4, prolactin fragment, Suramin, Suramin analogues, PPS, distamycin A analogues, FGF-2 Ab, antisense-FGF-2, Protamine, SU5416, soluble Fll-1, dominant-negative Flk-1, VEGF receptor ribosymes, VEGF ab, Aspirin, NS-398, 6-AT, 6A5BU, 7-DX, Genistein, Lavendustin A, and Ang-2.

In some embodiments of the present invention, the physical device can be deployed to be in direct contact with the vascular network 124 supplying the proliferative cells. In this manner, the physical device releases anti-proliferative agents directly into the vascular network 124 for delivery to the proliferative cells. Similarly, the physical device can release angiogenesis inhibitors into the blood stream to inhibit the extension of the vascular network 124 into the fibroid or the further expansion of the vascular network within the fibroid. As will be described in detail below, the physical device can comprise a variety of configurations including a stent for placement into the vascular network 124 and an external restricting member such as, for example, a clamp, a suture and a constricting band or clip. For female patients, the physical device can comprise a plurality of devices placed through transvaginal injection near the uterus including, for example, gel depots, degradable or bio-absorbable polymer depots, polymer rod inserts, T-shaped implants, vaginal rings and adhesive devices. Depending upon the configuration of the physical device, the physical device not only delivers the treatment drugs but also interacts directly with the vascular network 124 to limit blood flow, and consequently, oxygen flow to the proliferative cells to initiate hypoxic-ischemic conditions within the proliferative cells.

Figure 3:
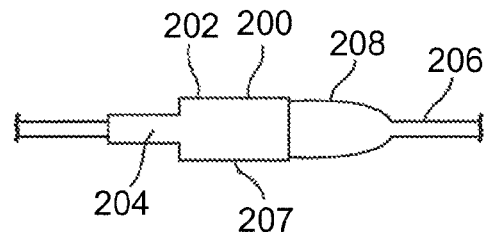
FIG. 3 is a plan view of an expandable occlusion stent positioned crimped over an inflation balloon of an inflation catheter.

As illustrated in FIG. 3, a representative physical device can include an occluding stent 200. Occluding stent 200 generally comprises an expandable body 202 defining a lumen 204. Expandable body 202 can comprise suitable materials including, for example, stainless steel, tantalum, MP35, iridium-titanium alloys and similar. Occluding stent can also be fabricated from biodegradable polymers. Examples of biodegradable or bio-absorbable polymers include polylactide (PLA), polylactide-co-glicolide (PLGA), polycaprolactone (PCL), polyanhydrides, polyglycolides (PGA), polyorthoesters (POE), polydioxanone, ethyl cellulose, hydroxyethyl cellulose, PLGA-PEG (polyethylene glycol) block copolymers, PLA-PEG block copolymers, PLC-PEG block copolymers, POE-PEG block copolymers, polyarylates, and polybutyrate. Occluding stent 200 can be crimped in place over a conventional balloon catheter 206 such that occluding stent 200 assumes a crimped state 207 having approximately ⅔ of the length of expandable body 202 residing over an inflatable balloon 208. In crimped state 207, occluding stent 200 can be steerably directed to a desired location in vascular network 124. Confirmation of the placement of occluding stent 200 can be accomplished utilizing a suitable medical imaging technology including, for example, computer axial tomography (CAT), magnetic resonance imaging (MRI), or transrectal ultrasound (TRUS). Alternatively, occluding stent 200 can comprise designs and methods as taught in U.S. Pat. No. 7,073,504 and U.S. Patent Publication No. 2005/0045183A1, both of which are commonly owned by the assignee of the present application, American Medical Systems of Minnetonka, Minn., and both of which are herein incorporated by reference in their entirety.

Figure 4:
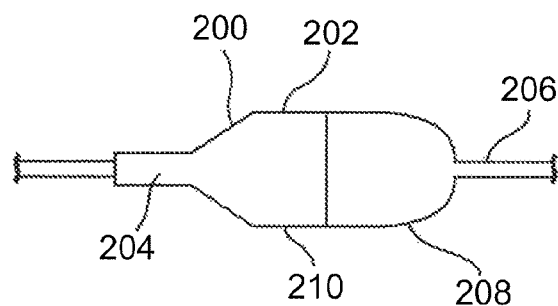
FIG. 4 is a plan view of the expandable occlusion stent of FIG. 3 inflated to an expanded state through inflation of the inflation balloon.
Figure 5:
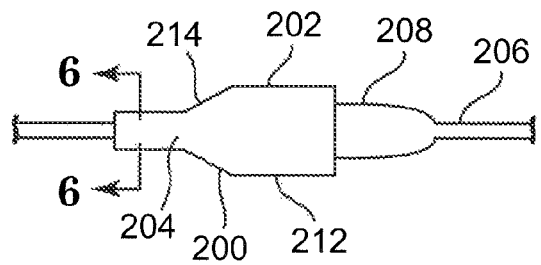
FIG. 5 is a plan view of the expandable occlusion stent of FIG. 3 in a cone-like 20 disposition following deflation of the inflation balloon.

Once occluding stent 200 is positioned, inflatable balloon 208 is inflated such that the portion of the expandable body 202 residing over inflatable balloon 208 is expanded such that occluding stent 200 assumes an expanded state 210 as shown in FIG. 4. As inflatable balloon 208 is subsequently deflated, occluding stent 200 assumes a deployed state 212 in which, the portion of expandable body 202 residing over the inflatable balloon 208 contracts slightly from expanded state 210 as shown in FIG. 5. Following deflation of inflation balloon 208, balloon catheter 206 can be withdrawn which leaving occluding stent 200 retained in place within the vascular network 124.

One or more treatment drugs 216 can be coated to expandable body 202 utilizing a variety of suitable processes including, for example, spraying, dipping, molding and the like. Preferably, the treatment drugs are coated to the occlusion stent 200 such that the one or more anti-proliferative agents can be dissolved and delivered to any non-mature proliferative cells that have commenced growth and proliferation initiated by exposure to the hypoxic/ischemic conditions induced with occlusion stent 200. Generally, the treatment drugs are delivered to the non-mature proliferative cells at a substantially reduced dosage level than that necessary for treatment of mature proliferative cells. In some embodiments, the treatment drugs can be administered at a dosage level of only a few hundred micrograms per day. As many of the treatment drugs, and especially the anti-proliferative agents, contemplated for use in shrinking or otherwise eliminating uterine fibroids 120 are extremely potent and in some cases, toxic, delivery of small doses over an extended period of time comprises a preferred method of administration.

In one representative embodiment, a 360° film can be formed surrounding occlusion stent 200. Occlusion stent 200 can be mounted upon a mandrel such that the occlusion stent 200 can be dipped into a polymer solution. The polymer solution can include the one or more treatment drugs dissolved within a solvent. Following one or more dips of the occlusion stent 200 into the polymer solution, expandable body 202 is essentially encased within a coating comprising the solvent and one or more treatment drugs. The solvent can be subsequently evaporated leaving the one or more treatment drugs coated to the expandable body 202.

In another representative embodiment, a similar dip-style process can be utilized in which the polymer solution includes a suitable porogen, preferably a water-soluble porogen. Following formation of a coating on the expandable body 202, the occlusion stent 202 can be dried, followed by immersion of the occlusion stent 202 in an aqueous solution to extract the porogen from the coating. Upon extraction of the porogen, occlusion stent 202 generally includes a porous film having interconnecting channels. The one or more treatment drugs can be dissolved in a solvent that will not dissolve the porous film and the occlusion stent can be immersed within the solvent. The occlusion stent 202 can then be removed and the solvent evaporated so as to leave behind the one or more treatment drugs filling the porous film.

As illustrated in FIG. 5, deployed state 212 can result in occluding stent 200 having a generally cone-shaped disposition 214 in which the portion of the expandable body 202 previously residing over inflatable body 208 has been expanded to essentially match the diameter of the vessel wall as shown in FIG. 6 while the portion of the expandable body that previously extended beyond inflatable body 208 remains at the diameter of crimped state 207. Cone-shaped disposition 214 causes the diameter of lumen 204 to narrow as blood flows through the occluding stent 200. With cone-shaped disposition 214, not only are the one or more anti-proliferative agents 216 delivered to uterine fibroid 120 but also the blood flow is reduced and consequently, the oxygen supply to uterine fibroid 120 is substantially reduced and/or eliminated. Upon inflicting hypoxic/ischemic conditions within uterine fibroid 120, the mature proliferative cells comprising uterine fibroid 120 suffer cellular death such that the now dead fibroid mass can be biologically resorbed by the body.

As illustrated in FIGS. 8, 9 and 10, a clamp 250 can be positioned and clamped over the vascular network 124, and more specifically, the uterine artery. Clamp 250 can comprise a one-piece body 252 having a hinge member 254 and a clasp member 256. Alternatively, clamp 250 can comprise a two-piece design having a pair of clasping ends for snapping the clamp 250 into position over the uterine artery. Inner surfaces 258 of clamp 250 can be coated or layered with one or more suitable treatment drugs 260 for diffusion through the vascular wall and into the bloodstream for delivery to the cells to be treated. When the treatment drug comprises at least one anti-proliferative agent, the anti-proliferative agent is delivered via the blood stream to proliferative cells to prevent further growth and shrink the proliferative cells. The treatment drug can also comprise angiogenesis inhibitors for minimizing the growth of the vascular system into the proliferative cells. Depending upon the design of hinge member 254, clamp 250 can further serve to limit blood flow to the fibroids 120. If hinge member 254 is of sufficient strength, clamp 250 can restrict blood flow to the fibroids 120, thereby initiating hypoxic/ischemic conditions which can further contribute to the treatment of the proliferative cells.

Referring to FIG. 11, a coated suture 260 or constricting band 262 can be deployed over the vascular network 124 and more specifically, the uterine artery in a similar manner as clamp 250. Coated suture 260 can comprise a length of conventional suture material being coated with one or more suitable treatment drugs while constricting band 262 can include a coating or layer on an inner surface of the constricting band. The coated suture 260 and constricting band 262 can both be tightened around the vasculature as desired to for positioning relative to the proliferative cells and to allow the one or more treatment drugs to diffuse through the vascular wall and enter the blood stream. When the treatment drugs comprise at least one anti-proliferative agent, the anti-proliferative agent(s) are delivered directly to the proliferative cell to prevent further grown and to shrink the proliferative cells. The treatment drugs can also comprise autogenesis inhibitors for inhibiting the growth the vascular systems within the proliferative cells. In some embodiments, the coated suture 260 and constricting band 262 can be tightened about the vasculature to restrict blood flow to the uterine fibroids 120 so as to induce hypoxic/ischemic conditions within the mature proliferative cells. In addition to the localized delivery of treatment drugs to uterine proliferative tissue by directly accessing the vascular network 124, some representative embodiments of the present invention can be positioned directly against the vaginal wall 111 such that treatment drugs can diffuse through the vaginal wall 111 and into the vascular network 124. Generally, the delivery mechanism can take the form of a coating or layer one or more treatment drugs applied to the physical device. In some alternative embodiments, the delivery mechanism can take the form of an injection or similar dispensing mechanism whereby the one or more treatment drugs can be delivered directly into the uterine proliferative tissue or alternatively, can be delivered to a region proximate the vascular network 124 for subsequent diffusion into the blood stream. In some embodiments, the physical device can be configured for vaginal deployment in a manner that applies pressure directly against the vaginal wall 111. In this minimally invasive manner, not only does the physical device allow for diffusion of the one or more anti-proliferative agents but also the pressure applied to the vaginal wall 111 can serve to physically occlude the vascular network 124 so as to initiate hypoxic/ischemic conditions within uterine proliferative cells.

Figure 12:
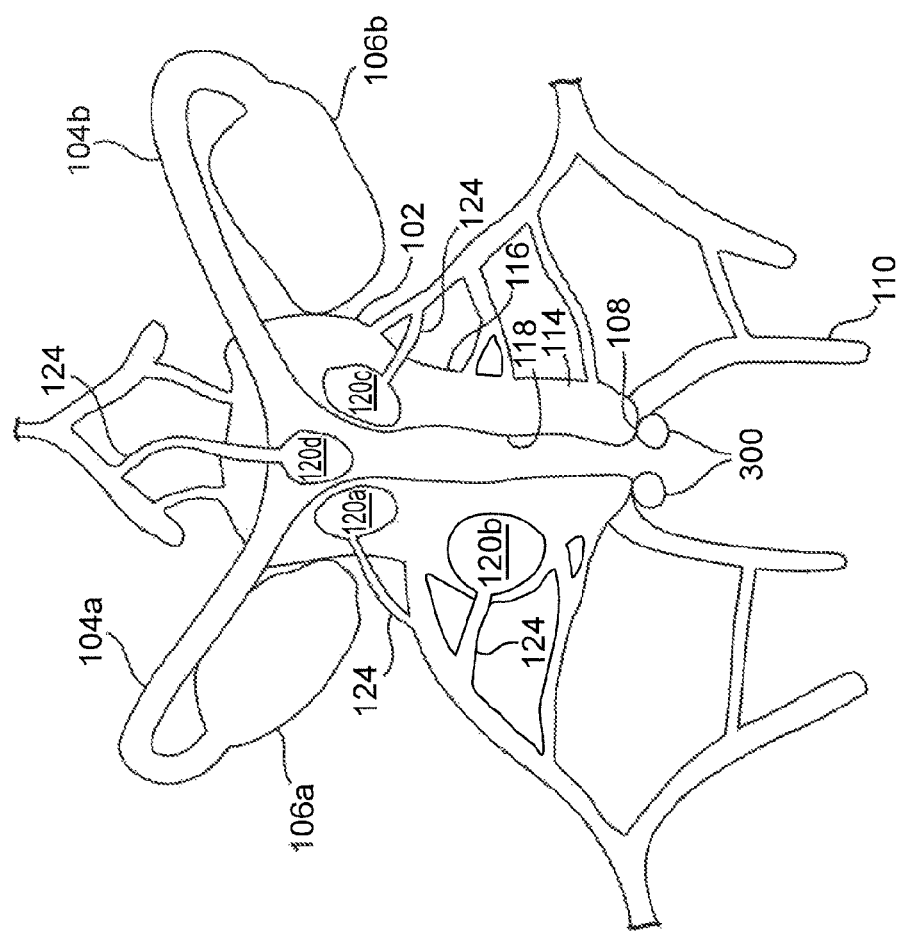
FIG. 12 is an illustration of a female reproductive system including a vaginally introduced device for treatment of uterine proliferative conditions.

As illustrated in FIG. 12, a vaginally introduced device 300, that is placed through transvaginal injection, can be placed within vagina 110 or uterus 102 such that one or more treatment drugs diffuses from the vaginally introduced device 300 and is absorbed through vaginal wall 111. Once the one or more treatment drugs been absorbed, vascular network 124 delivers the one or more treatment drugs to the uterine proliferative cells or inhibits the formation of the vascular network 124 itself so as to prevent further growth of the fibroid and shrink the proliferative cells.

Figure 13:
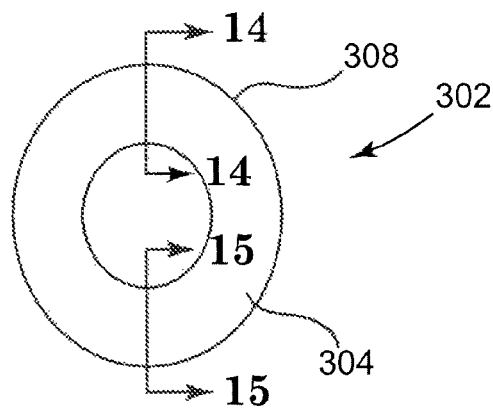
FIG. 13 is a plan view of a vaginal ring for treatment of uterine proliferative conditions.
Figure 14:
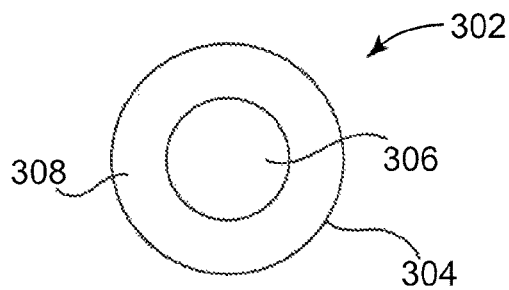
FIG. 14 is a section view of the vaginal ring of FIG. 13 taken at line 14-14 of FIG. 13 according to an embodiment of the invention.

As illustrated in FIGS. 13 and 14, vaginally introduced device 300 can comprise a vaginal ring 302 designed to reside against the cervix 108 and press outwardly against the vaginal wall 111. Alternatively, the vaginal ring 302 is designed to reside on top of, near and/or about the fibroid. In addition, an IUD may also be placed in the cervix having the treatment drugs thereon or somewhere therein. Vaginal ring 302 generally comprises a ring wall 304 having an internal ring 306 surrounded by a ring coating 308. In some embodiments, internal ring 306 can comprise a non-absorbable polymer such as, for example, silicone elastomers such as Silicone Elastomers VIII available from Nusil Technology, LLC of Carpinteria, Calif.; polyurethane elastomers, polyurethane and silicone copolymers, polystyrene-butadiene block copolymers and polycarbonates. Alternatively, internal ring 306 can comprise a non-absorbable polymer having one or more treatment drugs molded there within. In some embodiments, ring coating 308 can comprise a coating material including a polymer such as, for example, MED 4820 with one or more treatment drugs. Alternatively, ring coating 308 can comprise a porous polymeric coating acting as a rate controlling membrane for administering one or more treatment drugs molded with the internal ring 106. Various representative compositions of vaginal ring 302 are described in Table 1 below.

TABLE 1

Representative Compositions for Vaginal Ring 302

| Example | Internal Ring 306 | Ruing Coaring 308 |
| --- | --- | --- |
| 1 | Silicone Elastomer VIII (Nusil MED-4750) | MED4820 with 10 weight percent rapamycin |
| 2 | Silicone Elastomer VIII (Nusil MED-4750) | MED4820 with 10 weight percent rapamycin |
| 3 | Silicone Elastomer VIII (Nusil MED-4750) | MED4820 with 10 weight percent rapamycin |
| 4 | Silicone Elastomer VIII (Nusil MED-4750) | MED4820 with 10 weight percent rapamycin |
| 5 | Silicone Elastomer VIII (Nusil MED-4750) | MED4820 with 10 weight percent rapamycin |
| 6 | Silicone Elastomer VIII (Nusil MED-4750) | MED4820 with 30 weight percent rapamycin/10 weight percent PEG2000 |
| 7 | Silicone Elastomer VIII (Nusil MED-4750) | Silicone Elastomer VIII with 5 weight percent rapamycin |
| 8 | Silicone Elastomer VIII with 5 weight percent rapamycin | Silicone Elastomer VIII |

Figure 15:
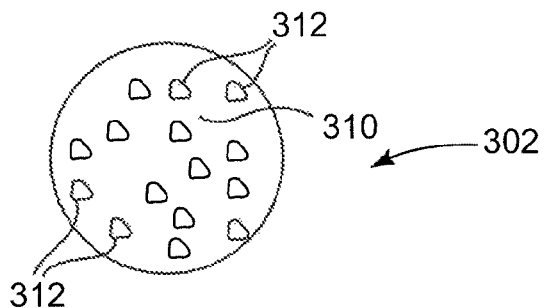
FIG. 15 is a section view of the vaginal ring of FIG. 13 taken at line 15-15 of FIG. 13 according to an embodiment of the invention.

Referring to FIG. 15, an alternative embodiment of vaginal ring 302 can comprise a single ring 310 lacking either a coating or internal ring but further including one or more treatment drugs in the form of a plurality of treatment drug particles 312. Treatment drug particles 312 having at least one anti-proliferative agent can comprise particles of one or more of rapamycin and rapamycin analogs. Alternatively, treatment drug particles 312 having at least one anti-proliferative agent can comprise podophyllotoxin, podophyllotoxin analogs, curcumin, halofuginone and 2-methoxyestradioL For example, single ring 310 can comprise a matrix design with 5% by weight rapamycin loading in MED4820. The treatment drug particles 312 can also comprise angiogenesis inhibitors for inhibiting the growth of the vascular network 124 into the fibroid.

Figure 56:
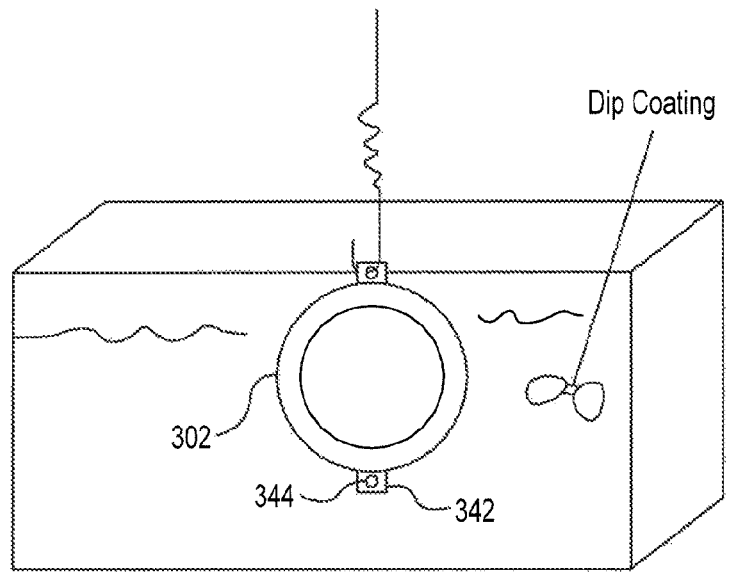
FIG. 56 is a representative view of the drug eluting intravaginal ring depicted in FIG. 49 being dipped within a treatment drug bath to apply a treatment drug to the intravaginal ring.
Figure 78:
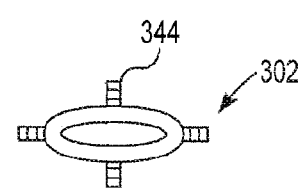
FIG. 78 is a perspective view of a drug eluting intravaginal ring having a plurality of extendable tabs for gripping the vaginal wall according to an embodiment of the present invention.

Referring to FIGS. 49-55, 61, 78 alternative embodiments of vaginal ring 302 comprise various retention assemblies 340 for preventing the vaginal ring 302 from being dislodged. As depicted in FIGS. 49-55, 61 the vaginal ring 302 can comprise at least one tab 342 for engaging the vaginal walls after implantation. The at least one tab 342 define aperture 344 for receiving a hook or a hanging means whereby the vaginal ring 302 can be dipped into a treatment drug solution to coat the vaginal ring 302 as shown in FIG. 56. As shown in FIG. 78, the vaginal ring 302 can comprise a plurality of spring loaded tines 346 adapted to expand after implantation to engage the vaginal walls after implantation.

Figures 57, 58:
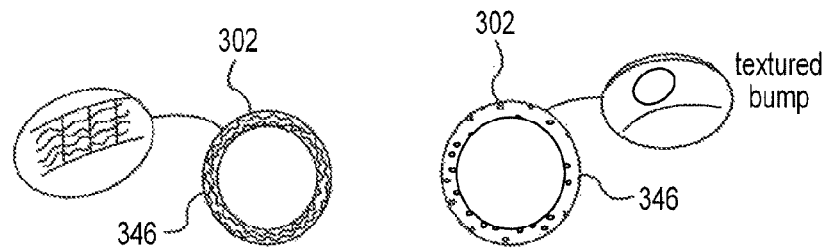
FIG. 57 is a side view of a drug eluting intravaginal ring having surface texturing according to an embodiment of the invention.
FIG. 58 is a side view of a drug eluting intravaginal ring having surface texturing according to an embodiment of the invention.

Referring to FIGS. 57-58, the vaginal ring 302 can comprise surface texturing 346 such as a plurality of bumps or corrugated for engaging the vaginal walls and epithelial ridges after implantation. The surface texturing is not limited to the vaginal ring 302 configuration and can be incorporated with various other forms of vaginal implants such as rod shaped implants. According to an embodiment of the invention depicted in FIGS. 62-63, the vaginal ring 302 can comprise a plurality of shaped ridges 347 molded on the exterior of the ring having a "sun fire" or "shark tooth" shape for gripping the vaginal walls. The shaped ridges 347 can be facing in the same direction or in opposite directions. Alternatively, the vaginal ring 302 can comprise bio adhesive applied to the exterior of the vaginal ring 302 to adhere the ring 302 to the vaginal walls. According to an embodiment of the invention depicted in FIGS. 64-65, the vaginal ring 302 can further comprise a plurality of approximating elements 349 extending from the vaginal ring 302 for gripping the vaginal walls. The approximating elements 349 can be facing the same direction or in opposite directions.

Figure 69:
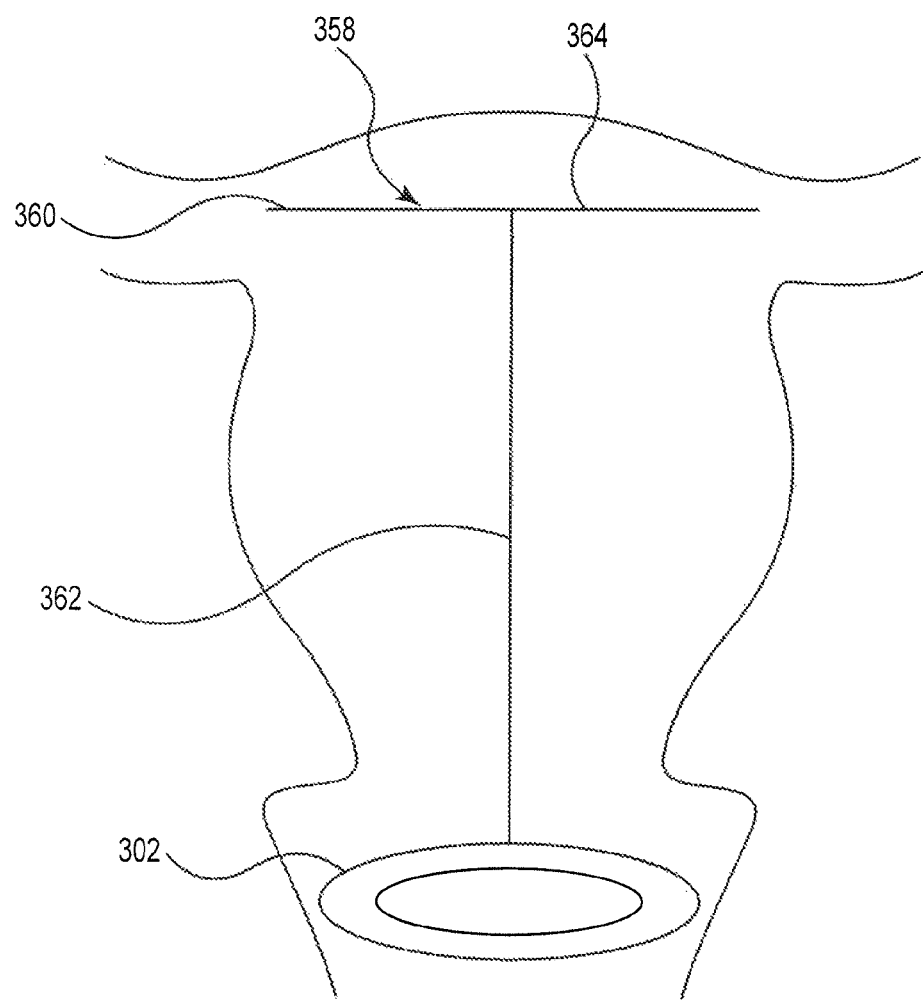
FIG. 69 is a representative view of a drug eluting intravaginal ring having an anchor assembly positioned within the uterine cavity.
Figure 70:
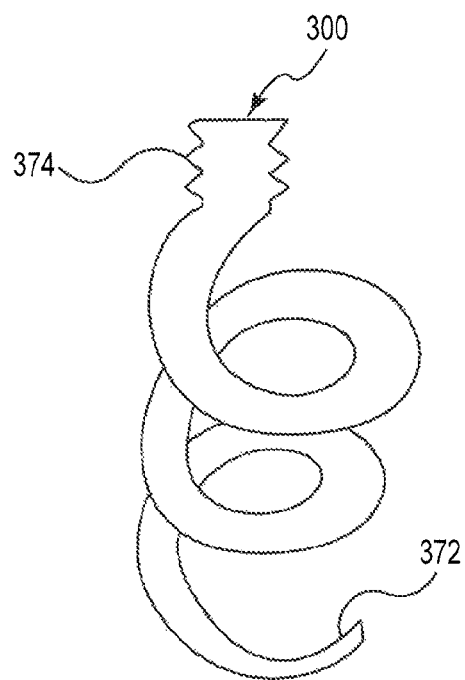
FIG. 70 is a side view of a vaginally introduced device for burrowing into the wall of a biological lumen.
Figure 71:
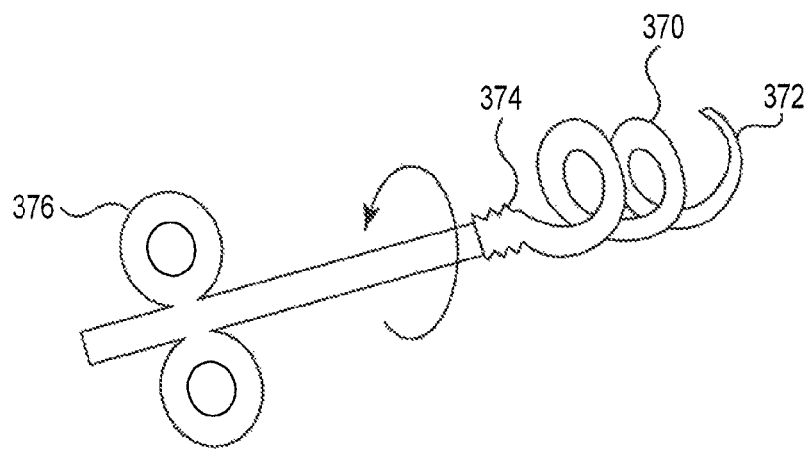
FIG. 71 is a perspective view of the vaginally introduced device of FIG. 70 engaged by an insertion tool for burrowing the vaginally introduced device into the wall of a biological lumen.
Figure 72:
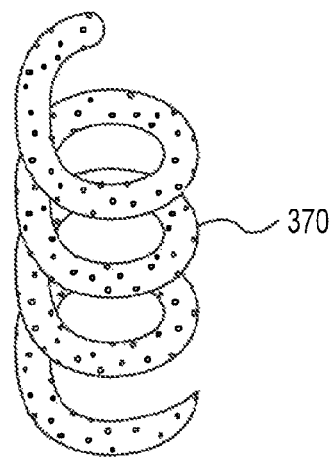
FIG. 72 is a side view of the vaginally introduced device of FIG. 72 having a topically applied treatment drug according to an embodiment of the present invention.
Figure 73:
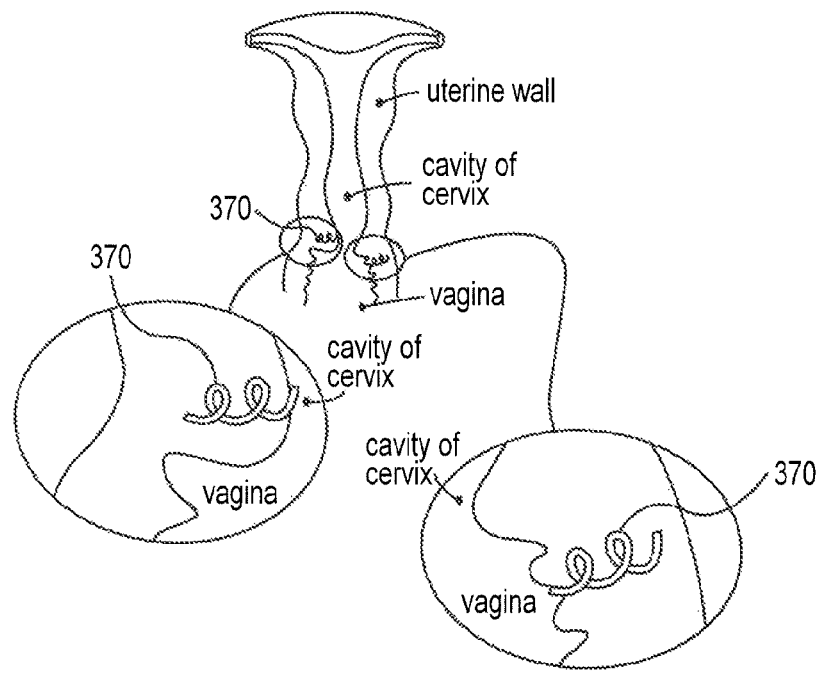
FIG. 73 is a representative view of the vaginally introduced device of FIG. 70 implanted in the wall of the uterine cavity and the vaginal cavity.

Referring to FIG. 69, alternative embodiments of the vaginal ring 302 include embodiments wherein the vaginal ring 302 is operably linked to an anchor 358. The anchor 358 can comprise a generally T-shape and have anchor arms 360 and a stem 362. The anchor arms 360 are inserted into the fallopian tubes 104a, 104b to anchor the vaginal ring 302. The stem 362 extends from the anchor arms 360 through the uterus 102 to the vaginal ring 302 in the vagina 110. Alternatively, treatment drugs can be applied to the anchor 358 and inserted into the uterus 102 without a vaginal ring 302 so as to directly supply treatment drugs to the uterus 102 rather than the vagina 110. According to an embodiment of the present invention, the stem 362 can further comprise a spring mechanism 364 for extending the stem 362 after implantation to ease implantation of the anchor 358.

Figures 59, 60, 61:
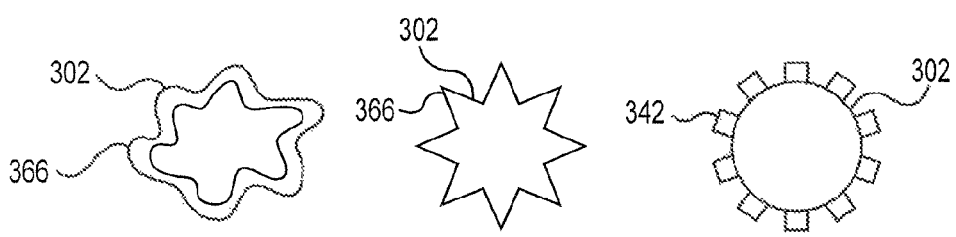
FIG. 59 is a side view of a drug eluting intravaginal ring having a plurality of protrusions according to an embodiment of the invention.
FIG. 60 is a side view of a drug eluting intravaginal ring having a plurality of protrusions according to an embodiment of the invention.
FIG. 61 is a side view of a drug eluting intravaginal ring having a plurality of protrusions according to an embodiment of the invention.

Referring to FIGS. 59-61, alternative embodiments of the vaginal ring 302 can include embodiments wherein the vaginal ring 302 comprises a variety of protrusions 366 for gripping the vaginal walls. The vaginal ring 302 can comprise memory shaped materials, such as nickel titanium allows, which expand or collapse depending on the temperature of the material.

To illustrate the effectiveness of the disclosed devices and methods, the vaginal ring embodiment was animal tested to test the efficacy of a localized, controlled release of treatment drugs to reduce the size of uterine fibroid (leiomyoma) formation in nude mice. The treatment drugs used in this test included an anti-proliferative agent. The subject size comprised forty eight, 8-10 week-old, female mice. Each mouse was implanted with the leiomyoma-derived cell line, ELT-3, that produce tumors with a short latency when injected in nude mice. The forty eight mice were divided into three groups and cell suspensions in either medium (serum free DF8 medium) or Matrigel were prepared at the concentrations indicated in Table 2 below.

TABLE 2

Group Information for Anti-Proliferative Testing of Female Mice

| Group # | # of Animals | Treatment | Cell # in 200 μL per site (2 sites per animal) |
|---|---|---|---|
| 1 | 24 | Medium | $2 \times 10^6$ |
| 2 | 12 | Martigel | $4 \times 10^4$ |
| 3 | 12 |  | $2.5 \times 10^5$ |

200 μl, of the indicated cell preparations were injected subcutaneously above each hip. Five to 9 days before inoculation, the mice were anesthetized and implanted with pellets of 17—-estradiol (one 1.7 mg 60-day release tablets in each mouse, Innovative Research, Sarasota, Fla.). The estradiol pellet was implanted subcutaneously in the interscapular area. The pellet was implanted using either a Trocar or surgically placed in a pocket formed between the skin and the muscle. Fresh pellets were implanted 8 weeks after initial implantation.

Following implantation, the mice were recovered, and observed weekly post-injection for tumor formation. Resulting tumors were measured (length×width) weekly with a calibrated caliper. Formation of tumors was observed weekly for up to 13 weeks or when the tumors grow to a diameter of approximately 0.75-1.0 cm. At that time, ring 302 was implanted into half the mice to test its ability to reduce tumor size through the controlled release of the anti-proliferative agent rapamycin, with the remaining mice receiving a control consisting of the ring 302 absent the rapamycin. The ring 302 was implanted by surgical subcutaneous implantation alongside, on top of or around the tumor. Tumors were measured (length×width) weekly with a calibrated caliper for an additional 10 weeks. At 23 weeks, the mice were humanely euthanized, tumors observed, measured and removed and placed in 10% formalin for histopathology processing and the ring 302 was retrieved for determination of the remainder of drug in the device.

Under the conditions of this testing, the cell line did form un-encapsulated malignant spindle cell tumors at the injection site of all the test and control mice examined microscopically. When the ring 302 was implanted onto the malignant tumors induced by the Eker Rat Leiomyoma Cell Line, there were larger amounts of ovoid/round cells, pleomorphism, anisokaryosis, bizarre nuclei, necrosis, hemorrhage, and mast cells in the control masses, and larger amounts of fibrosis and vascularization in the test masses. It is believed that the control masses had larger amounts of changes in the cells, nuclei and overall tumor elements because these masses were not treated with the rapamycin as the test masses were. An increase in the amount of fibrosis and vascularization in the test masses was likely found because these masses were treated and these reactions were secondary to the treatment with the rapamycin. No microscopic lesions were found in the uterine tissue that could be attributed to the test material. Changes found in the reproductive organs of the mice were considered secondary to the normal estrus cycle of females.

Figure 16:
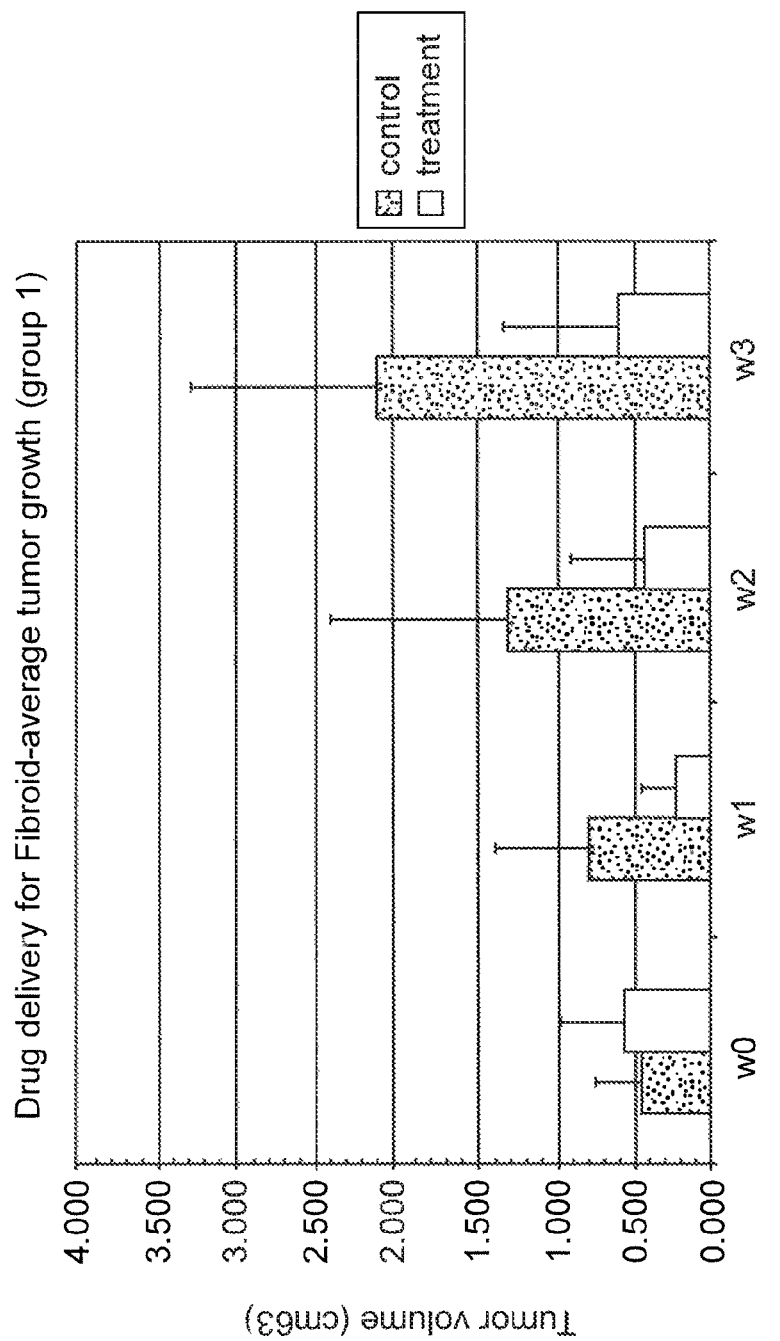
FIG. 16 is a chart illustrating effectiveness of an implanted vaginal ring having rapamycin on fibroid tumor growth results for Group I control and test group mice previously implanted with Eker rat leiomyoma CELT3) cell line cells.
Figure 17:
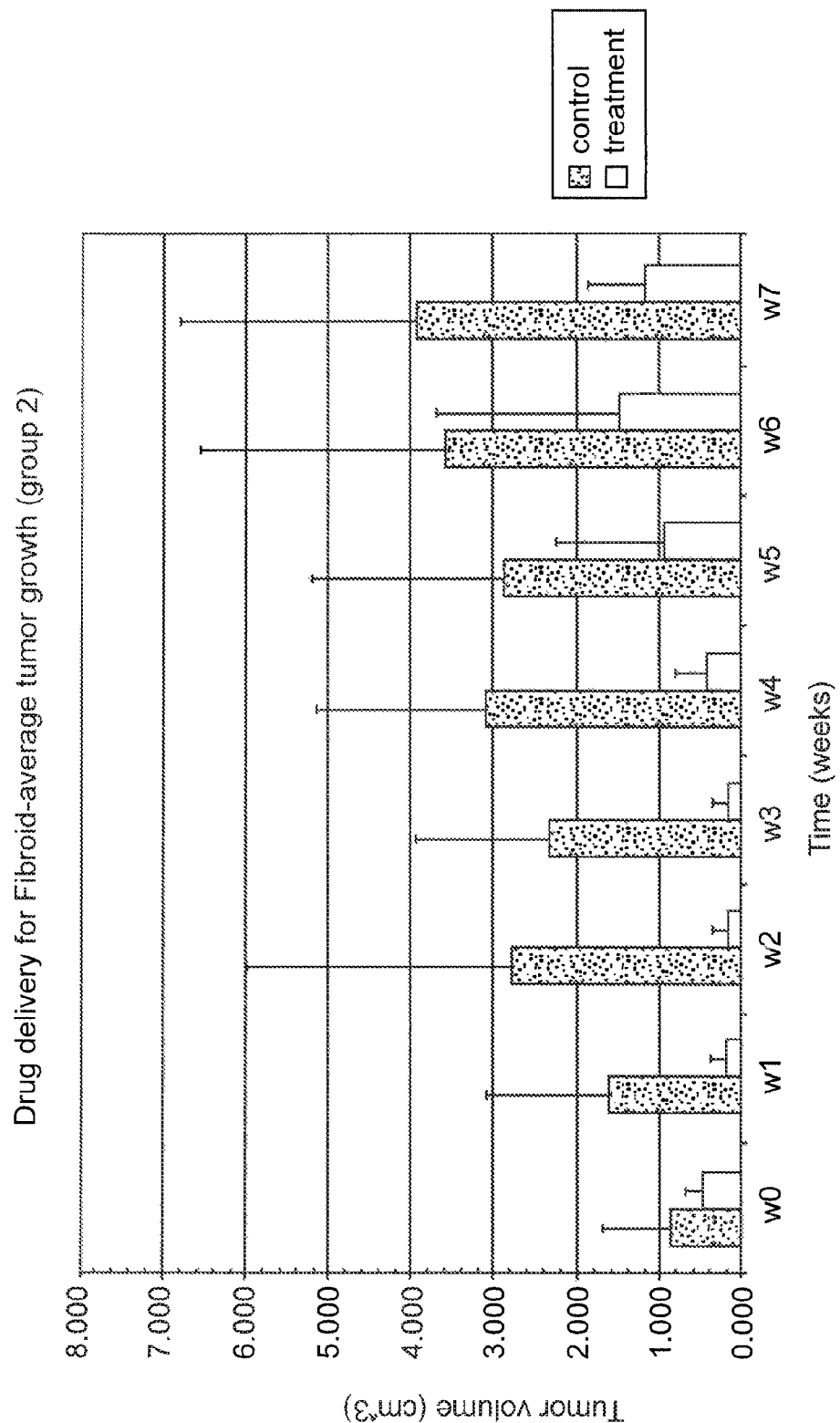
FIG. 17 is a chart illustrating effectiveness of an implanted vaginal ring having rapamycin on fibroid tumor growth results for Group II control and test group mice previously implanted with Eker rat leiomyoma (EL T3) cell line cells.
Figure 18:
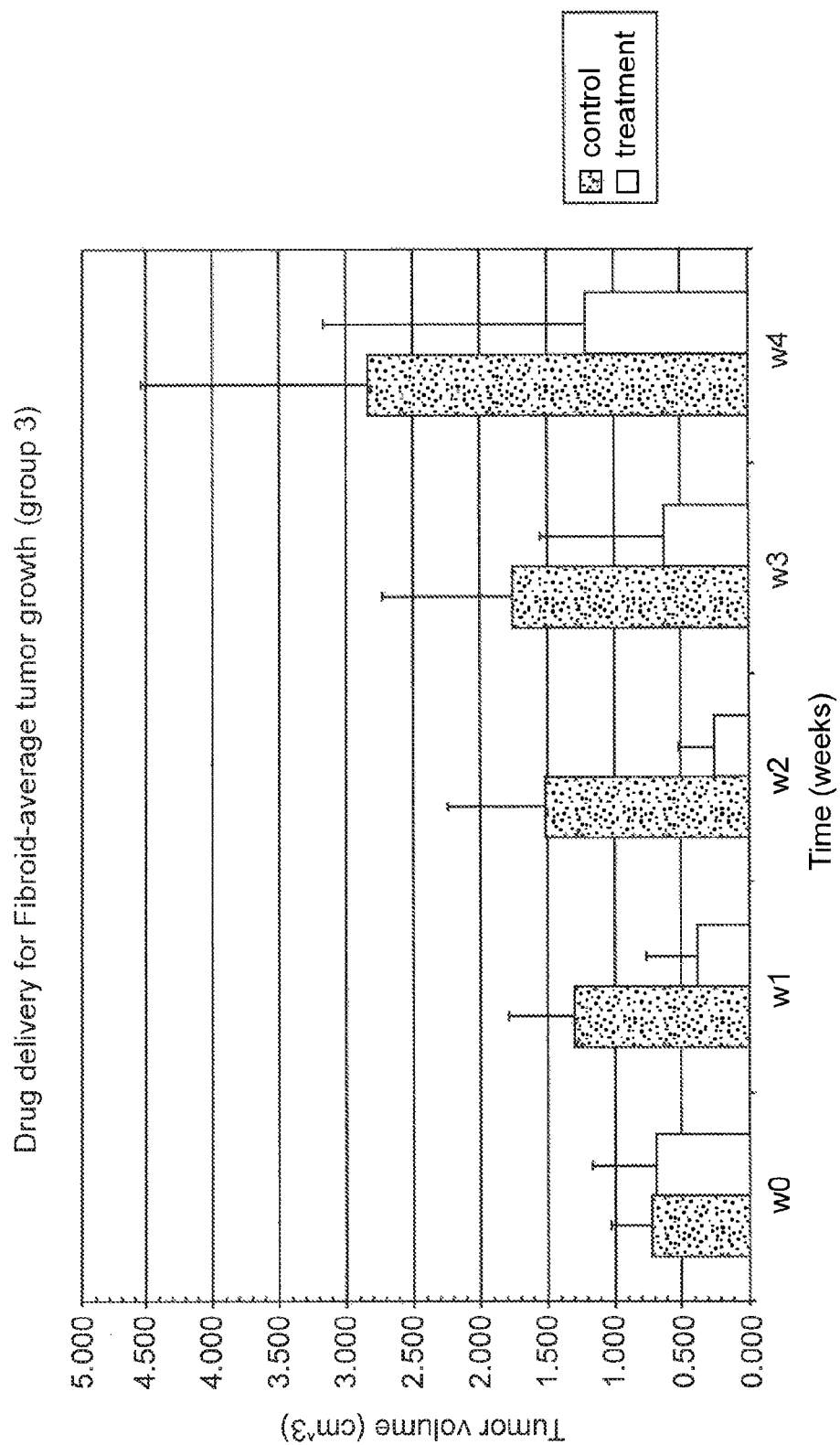
FIG. 18 is a chart illustrating effectiveness of an implanted vaginal ring having rapamycin on fibroid tumor growth results for Group III control and test group mice previously implanted with Eker rat leiomyoma CELT3) cell line cells.
Figure 19:
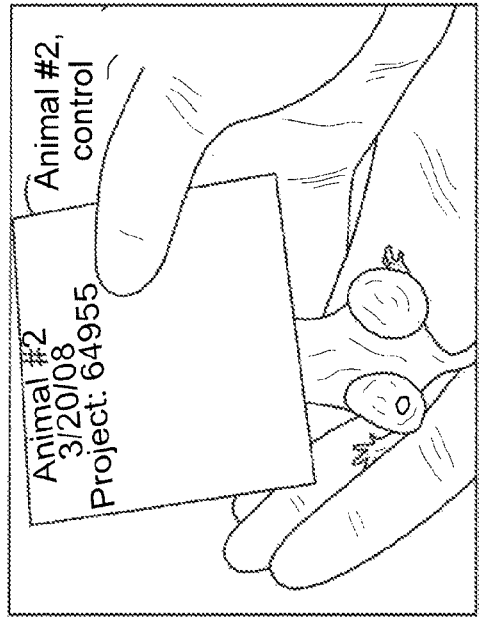
FIG. 19 is a photograph visually depicting fibroid tumor size for a non-treated control mouse previously implanted with Eker rat leiomyoma (ELT3) cell line cells.
Figure 20:
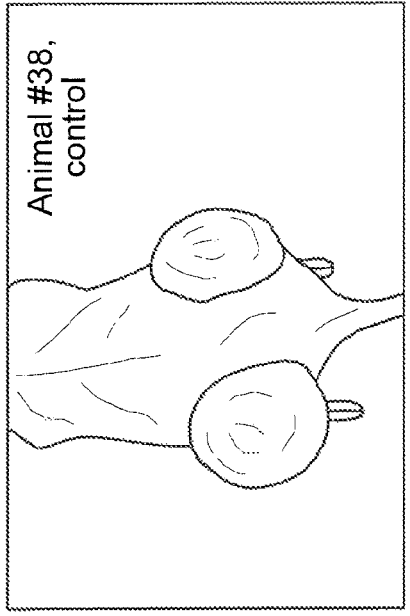
FIG. 20 is a photograph visually depicting fibroid tumor size for a non-treated control mouse previously implanted with Eker rat leiomyoma CELT3) cell line cells.
Figure 21:
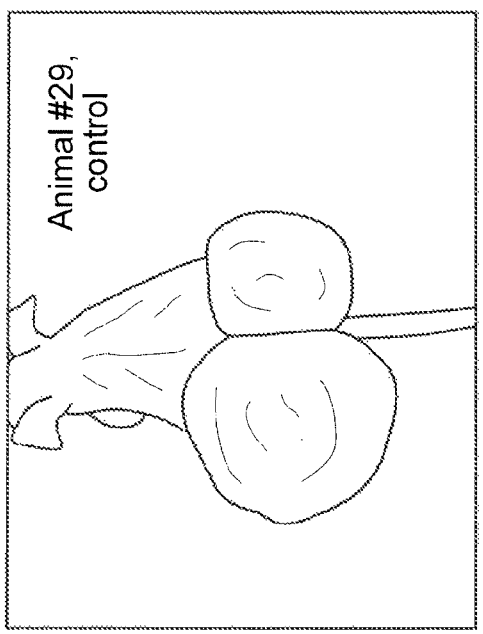
FIG. 21 is a photograph visually depicting fibroid tumor size for a non-treated control mouse previously implanted with Eker rat leiomyoma (EL T3) cell line cells.
Figure 22:
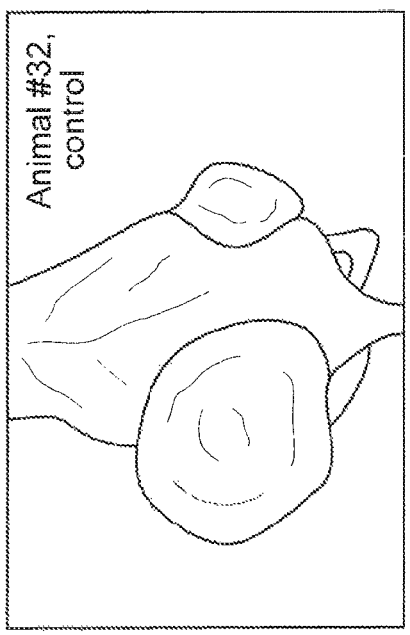
FIG. 22 is a photograph visually depicting fibroid tumor size for a non-treated control mouse previously implanted with Eker rat leiomyoma CELT3) cell line cells.
Figure 23:
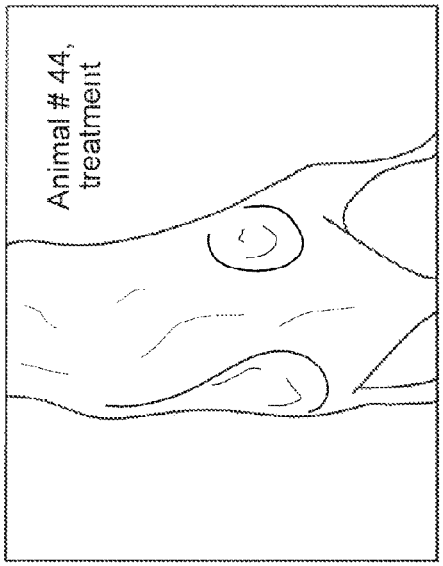
FIG. 23 is a photograph visually depicting fibroid tumor size for a locally administered, rapamycin treated test mouse previously implanted with Eker rat leiomyoma (EL T3) cell line cells.
Figure 24:
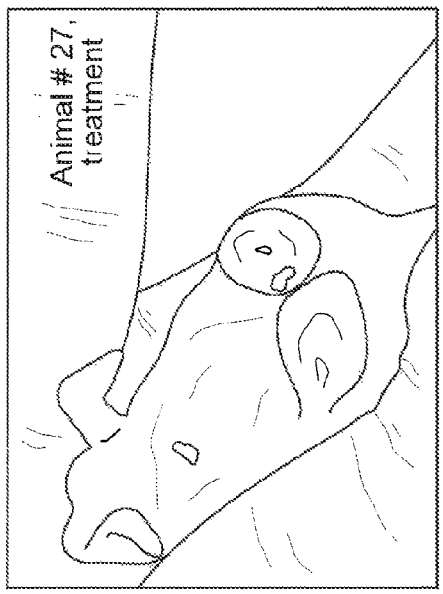
FIG. 24 is a photograph visually depicting fibroid tumor size for a locally administered, rapamycin treated test mouse previously implanted with Eker rat leiomyoma CELT3) cell line cells.
Figure 25:
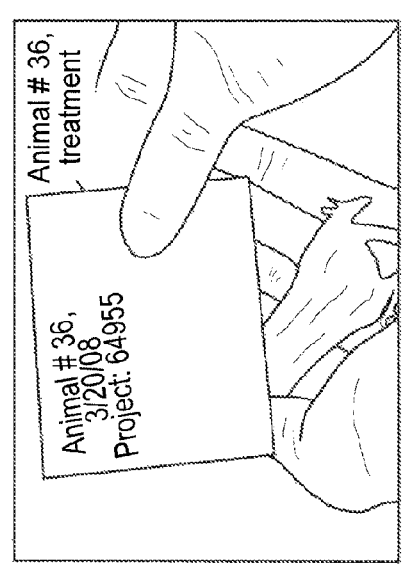
FIG. 25 is a photograph visually depicting fibroid tumor size for a locally administered, rapamycin treated test mouse previously implanted with Eker rat leiomyoma (ELT3) cell line 30 cells.
Figure 26:
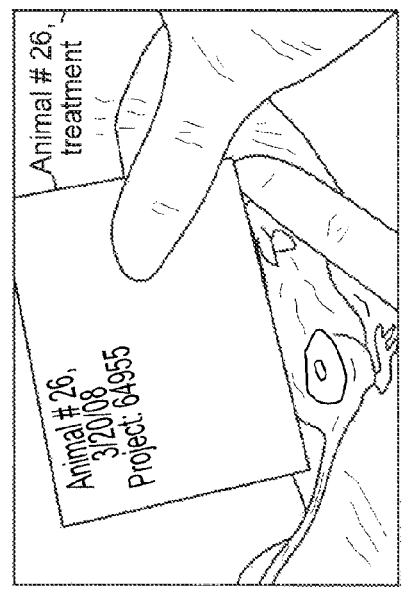
FIG. 26 is a photograph visually depicting fibroid tumor size for a locally administered, rapamycin treated test mouse previously implanted with Eker rat leiomyoma (ELT3) cell line cells.

Results illustrating the effectiveness of localized, controlled release of rapamycin with ring 302 for Groups 1, 2 and 3 are contained in FIGS. 16, 17 and 18 respectively. As illustrated, the size of the measured tumors decreased from their initial sized in each test group following implantation of ring 302, and consequently, following the localized absorption/diffusion of rapamycin into the tumors while tumor size continued to increase for the control group. While subsequent tumor size did increase after Week 1 for the test Group 1 mice, after Week 3 for test Group 2 mice and after Week 2 for Group 3 mice, the tumors size remained less than all of the corresponding control group mice. The later increase in tumor size for the test groups can be attributed to the rapamycin being depleted faster than expected in some mice. The depletion of the rapamycin and resulting loss of efficacy can be addressed in a variety of ways including increasing the initial localized doses, fine tuning of the release duration of the ring 302 to release over a longer period of time or by providing a release system having a bolus release at a beginning stage and then a subsequent slower release above the inhibition level for an extended period of time. In addition, implantation of an additional ring 302 at a time subsequent to the original implantation can also be used to prevent later tumor growth. Overall, the results indicate that localized, controlled delivery of an anti-proliferative agent such as rapamycin is an effective treatment for uterine fibroids. For purposes of illustration, random photographs for individual mice illustrating the difference in tumor size and growth between control mice are shown in FIGS. 19, 20, 21 and 22 whereas test mice receiving rapamycin by way of ring 302 are shown in FIGS. 23, 24, 25 and 26.

To illustrate the effectiveness of treatment drug combinations of anti-proliferative agents and autogenesis inhibitors, treatment drug combinations having at least one anti-proliferative agent, such as rapamycin, and at least one autogenesis inhibitor, such as curcumin or 2-methoxyestradiol, were tested on nude mice to determine the effectiveness of drug combinations at preventing the growth of proliferative cells in mice. The number of proliferative cells was measured on day 1, 5 and 8 of the experiment. As shown in Table 3, the treatment drugs comprising combinations anti-proliferative agents and autogenesis inhibitors were effective at minimizing the growth of proliferative cells as compared to the control sample and treatment drugs comprising only anti-proliferative agents. The combination of anti-proliferative agents and autogenesis inhibitors even lowered the amount of proliferative cells or eliminated the proliferative cells altogether.

TABLE 3

Representative cell counts demonstrating the effectiveness of treatment drugs comprising both anti-proliferative agents and autogenesis inhibitors.

|  | Day 1 | Day 5 | Day 8 |
| --- | --- | --- | --- |
| Cells Alone | 40000 | 175000 | 1292000 |
| DMSO 1:1000 | 40000 | 170833 | 1320000 |
| DMSO 1:10$^6$ | 40000 | 175000 | 1373333 |
| DMSO: Curc 1 □M | 35000 | 172500 | 1400000 |
| 5 nM Rapa | 36667 | 24167 | 40000 |
| 10 nM Rapa | 35000 | 26667 | 46666.67 |
| 5 nM 2-ME | 35000 | 171667 | 1386667 |
| 10 nM 2-ME | 35000 | 150833 | 1553333 |
| 10 nM Curc | 50000 | 155833 | 933333.3 |
| 1 □M Curc | 23333 | 41250 | 720000 |
| 5 nM Rapa, 10 nM Curc | 16667 | 17500 | 40000 |
| 5 nM Rapa, 1 □M Curc | 13333 | 12917 | 27500 |
| 10 nM Rapa, 10 nM Curc | 20000 | 13750 | 45833.33 |
| 10 nM Rapa, 1 □M Curc | 13333 | 11250 | 23333.33 |
| 5 nM Rapa, 5 nM 2-ME | 20000 | 12500 | 0* |
| 5 nM Rapa, 10 nM 2-ME | 10000 | 14583 | 0* |
| 10 nM Rapa, 5 nM 2-ME | 13333 | 12222 | 42500 |
| 10 nM Rapa, 10 nM 2-ME | 10000 | 13333 | 45000 |

*Proliferative cell count was below detectable levels.

Figure 27:
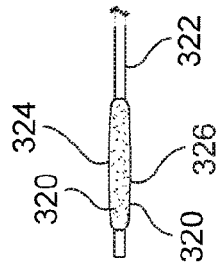
FIG. 27 is a plan view of a vaginally introduced inflation balloon for treatment of uterine proliferative conditions in an insertion disposition.
Figure 28:
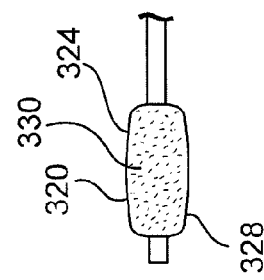
FIG. 28 is a plan view of the vaginally introduced inflation balloon of FIG. 27 for treatment of uterine proliferative conditions in an inflated disposition.
Figure 29:
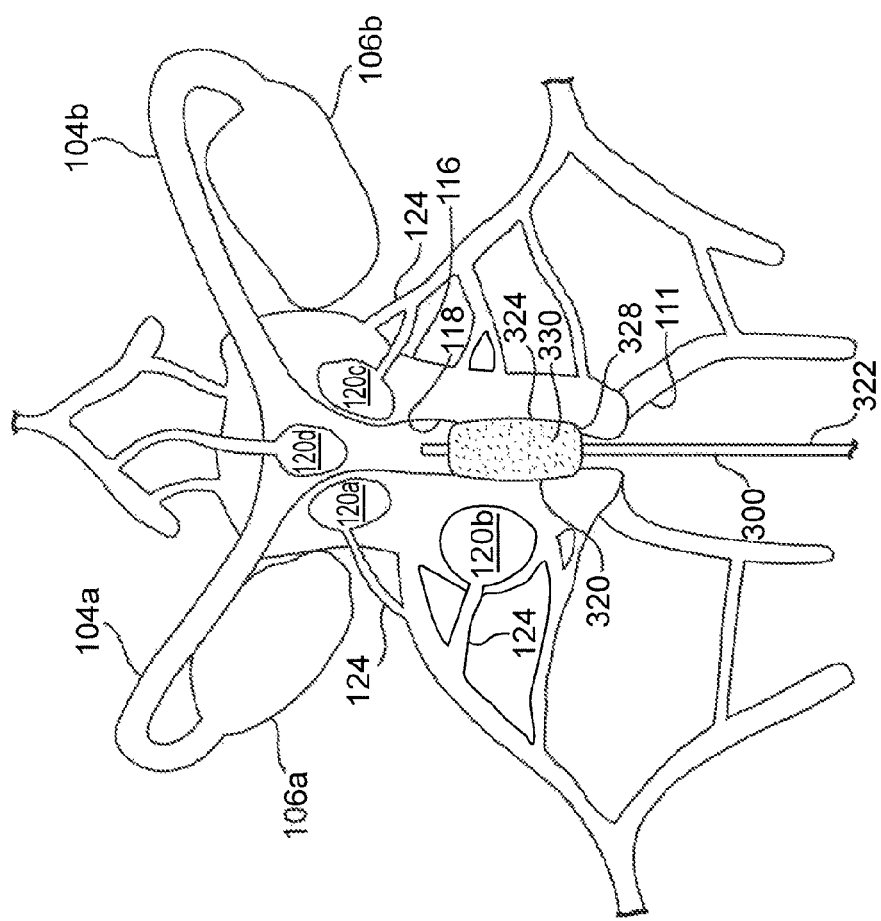
FIG. 29 is an illustration of a female reproductive system including a vaginally introduced device for treatment of proliferative cellular conditions.

As illustrated in FIGS. 27, 28 and 29, another alternative embodiment of vaginally introduced device 300 can comprise an inflation balloon 320 operably mounted over a catheter 322. Inflation balloon 320 generally comprises an inflatable body 324 capable of inflating from a non-deployed insertion disposition 326 to a fully deployed occlusion disposition 328 using a suitable inflation fluid. When inflation balloon 320 is in fully inflated disposition 328, inflatable body 324 presses outwards against the endometrium 118. Inflation balloon 320 further comprises an external coating 330 or layer of treatment drugs comprising an anti-proliferative agent such as rapamycin that diffuses through the endometrium 118 and into the vascular network 124 or alternatively, directly into uterine fibroids 120 that are in physical contact with the inflatable body 324. The anti-proliferative agent disrupts and/or eliminates any growth of the proliferative cells. The treatment drugs can also comprise autogenesis inhibitors for limiting or preventing the growth of the vascular network 124 into the fibrid. In some embodiments, inflation balloon 320 in the fully inflated disposition 328 can sufficiently press against the endometrium 118 so as to at least partially occlude the vascular network 124. With vascular network 124 occluded, hypoxic/ischemic conditions can be introduced to fibroids 120 to further assist with shrinking or otherwise killing the proliferative cells.

As illustrated in FIGS. 70-73, an alternative embodiment of vaginally introduced device 300 can comprise a burrowing implant 370 implantable in the vaginal or uterine wall. The corkscrew shape maximizes the surface area of the burrowing implant 370 to maximize the amount of drugs coated on the surface of the implant 370. The burrowing implant 370 can comprise a corkscrew shape having a pointed end 372 for burrowing into the vaginal wall and an engagement end 374 for engaging an insertion tool 376. The insertion tool 376 is adapted to rotate the borrowing implant 370 to screw the burrowing implant 370 into the vaginal wall. As shown in FIG. 2, the borrowing implant 370 can be coated with treatment drugs or comprise a biodegradable or bio-absorbable polymers encapsulating or contacting treatment drugs that diffuse through the vaginal walls into the vascular network 124.

As illustrated in FIGS. 66-68, an alternative embodiment of vaginally introduced device 300 can comprise a contoured implant 380 comprising a proximate end 382 and a distal end 384 wherein the proximate end 382 of the countered implant 380 comprises a larger cross-sectional area than the distal end 384. The contoured implant 380 can comprise a light bulb shape, kidney bean or triangular shape such that the contoured implant 380 fits the general shape of the vagina 110.

Figure 74:
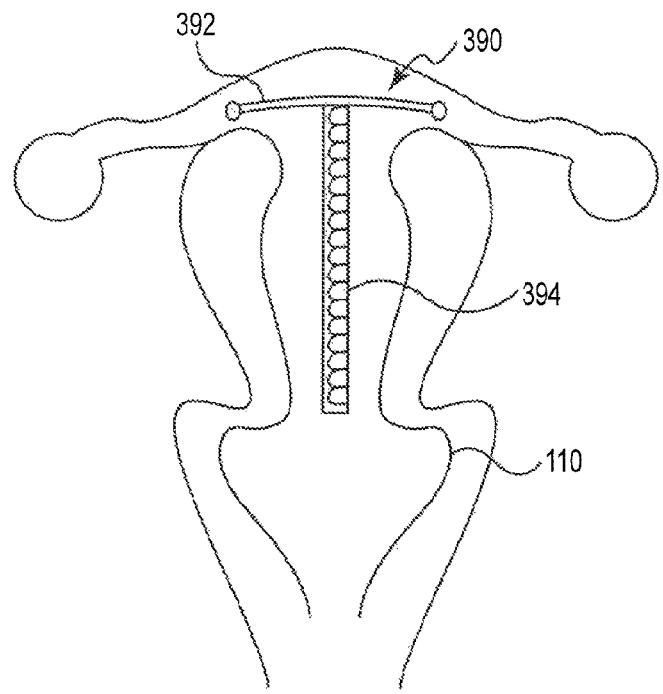
FIG. 74 is a representative view of a t-shaped implant according to an embodiment of the present invention positioned within the uterine cavity.
Figure 75:
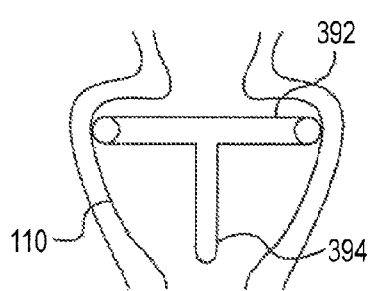
FIG. 75 is a representative view of a t-shaped implant according to an embodiment of the present invention positioned within the vaginal cavity.
Figure 76:
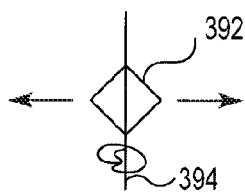
FIG. 76 is a side view of a t-shaped implant wherein the arms of the t-shaped implant are in the retracted position.
Figure 77:
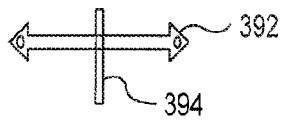
FIG. 77 is a side view of a t-shaped implant wherein the arms of the t-shaped implant are in the extended position.

Referring to FIGS. 74-76, an alternative embodiment of vaginally introduced device 300 can comprise a T-shaped implant 390 inserted into the vagina 110. The T-shaped implant 390 comprises anchor arms 392 for gripping the vaginal walls and a stem 394. The entire T-shaped implant 390 or only the stem 394 can be coated with the treatment drug. In an embodiment of the present invention, the anchor arms 392 can adjusted in length to insure the T-shaped implant 390 effectively grips the vaginal walls.

Figure 30:
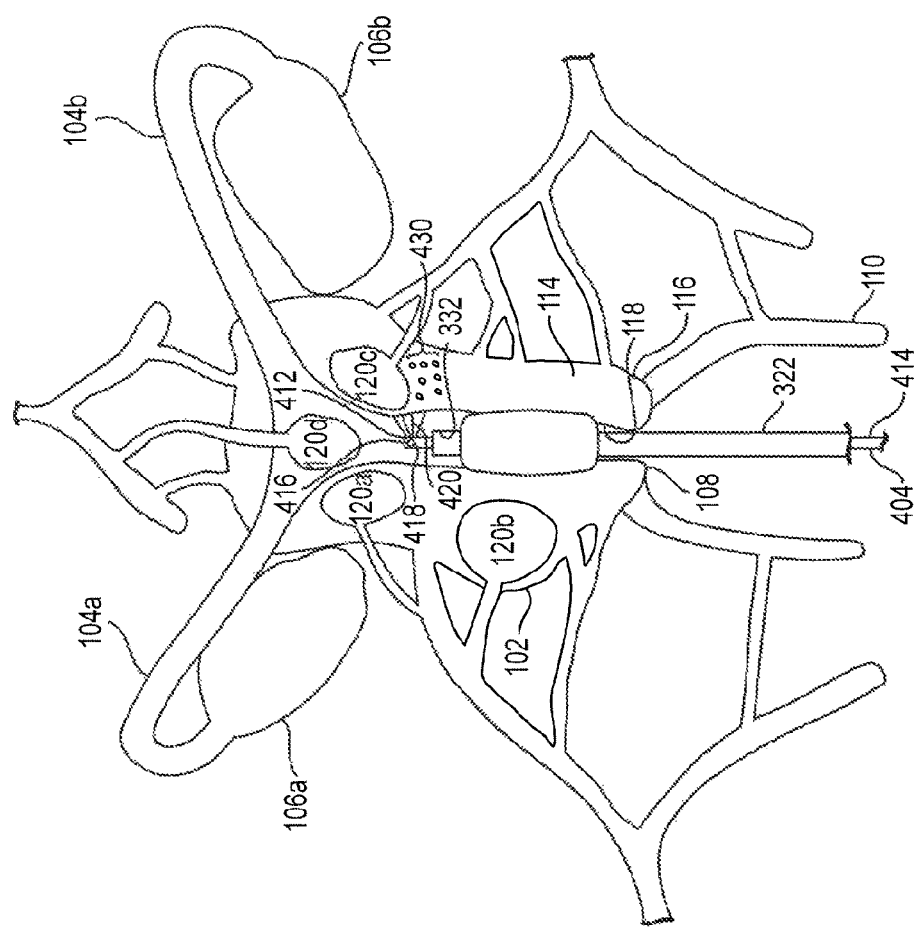
FIG. 30 is an illustration of a female reproductive system including a vaginally introduced device for treatment of proliferative cellular conditions.

In some alternative embodiments, inflation balloon 320 and catheter 322 can be used in combination with a high-pressure fluid injection system 400 as shown in FIG. 30 to deliver one or more treatment drugs through the endometrium 118 for absorption into the vascular network 124 or directly into the uterine fibroid 120. A representative high-pressure fluid injection system is illustrated generally in FIG. 31 and can comprise systems as described in International Publication No. 2007/079152A2 and commercially available from American Medical Systems of Minnetonka, Minn. Generally, high-pressure fluid injection system 400 can comprise an injector 402 and an applicator lumen 404. Injector 402 can comprise a manually activated syringe 401 or alternatively, an automated injector 403 including a user interface 406 and a connector member 408. User interface 406 can comprise an input means for selectively delivering one or more therapeutic agents in the form of a pressurized fluid through the connector member 408. Representative input means can include foot pedal 407, switches, buttons or a touch-screen capable of receiving touch commands as well as displaying system information including a mode of operation as well as operating parameters.

Figure 31:
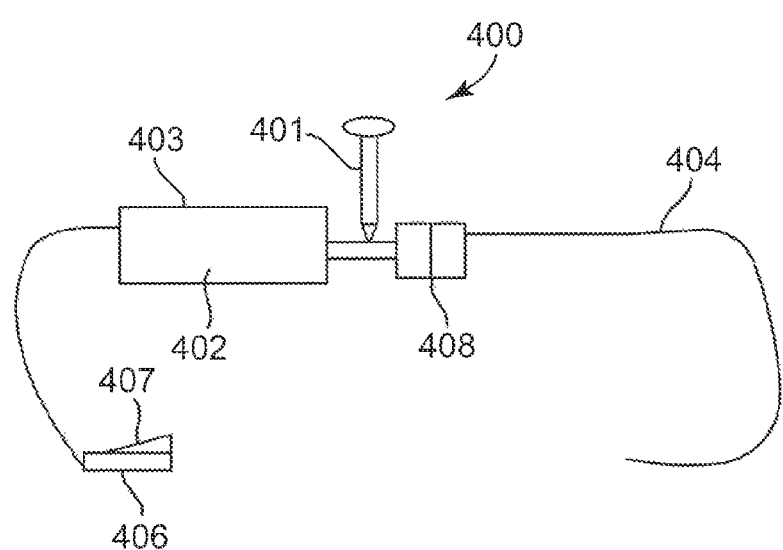
FIG. 31 is an illustration of a high pressure fluid injection system.

Referring to FIG. 31, applicator lumen 404 can comprise a non-metal, polymeric tube like device 412 having a proximal attachment end 414 and a distal treatment end 416. Nonmetal, polymeric tube like device 412 has a tube length of sufficient length to allow distal treatment end 416 to be advanced past a distal tip 332 of catheter 322. Non-metal, polymeric tube like device 412 is generally formed so as to have a burst strength of at least about 2,000 psi. In a preferred embodiment, the non-metal, polymeric tube like device 412 is formed to have a burst strength ranging from about 2,000 psi to about 5,000 psi. In one representative embodiment, non-metal, polymeric tube like device 412 is formed of a single high strength polymer such as, for example, a polyimide, polyetherimide available from General Electric under the trade name Ultem® and linear aromatic polymers such as PEEK™ available from Victrex plc. Alternatively, the non-metal, polymeric tube like device 412 can be formed from a reinforced polymer that is reinforced with materials such as, for example, nano-particles, clays or glass. In another embodiment, the non-metal, polymeric tube like device 412 is reinforced with a polymeric material such as, for example, a Kevlar, carbon or other suitable high strength polymeric fiber braided within the non-metal, polymeric tube like device 412. Generally, the non-metal, polymeric tube like device 412 is extruded though other appropriate fabrication methods including molding can be utilized as well.

As illustrated in FIG. 30, non-metal, polymeric tube like device 412 can be configured to deliver the one or more treatment drugs to a desired location within female reproductive tract 100. Distal treatment end 416 is generally advanced through the catheter 322 and past the distal tip 332 to gain access to the uterine cavity 112 as desired. In positioning the non-metal polymeric tube-like device 412 at a desired treatment location, it will be understood that a medical professional frequently employs a medical imaging system such as, for example, computer axial tomography (CAT), magnetic resonance imaging (MRI), or transrectal ultrasound (TRUS) so as to achieve the desired position of an administration orifice 418. Through the use of a medical imaging system, a medical professional can verify that administration orifice 418 is arranged for injection of the one or more therapeutic fluids at the desired treatment location.

Once the distal treatment end 416, and more specifically, the administration orifice 418 is positioned with respect to the desired treatment location, the injector 402 can be actuated so as to begin delivery of the one or more treatment drugs. Generally, injector 402 directs the one or more treatment drugs through the non-metal, polymeric tube-like device 412 at low velocities and high pressures generally between about 2,000 psi to about 5,000 psi. The high pressures supplied by the injector 402 are necessary due to the pressure losses experienced in the relatively, small diameter non-metal, polymeric tube like device 412. As the one or more anti-proliferative agents reaches distal treatment end 416, the one or more anti-proliferative agents are rapidly accelerated through the administration orifice 418 to form a fluid jet 420. Using fluid jet 420, the one or more treatment drugs can be controllably dispensed directly through the vaginal wall Ill, uterine wall 114 or into uterine fibroid 120 so as to reduce the potential for exposure to other non-desired areas. As the fluid jet 420 moves away from the administration orifice 418, the velocity and pressure of fluid jet 420 rapidly decreases.

In utilizing high-pressure fluid injection system 400, the one or more treatment drugs can comprise suitable liquid solutions or alternatively, the one or more treatment drugs can comprise microspheres or nanospheres of encapsulated anti-proliferative agent 430 capable of being transported within a suitable carrier fluid. Generally, encapsulated treatment drugs 430 comprises one or more liquid or gel-based agents retained surrounded by a bio-absorbable shell. The bio-absorbable shell can comprise a suitable bio-absorbable material selected so as to avoid degradation and within carrier fluid. Representative bio-absorbable materials can include, for example, PLGA, PLA, PCl, polyhydroxybutyrate, poly-orthoesters, polyoxyethylenes and copolymers of these.

In some alternative embodiments, inflation balloon 320 and catheter 322 can be used in combination with an insertion rod 500 to deliver one or more treatment drugs into the fibroid 120 or vascular network 124 as shown in FIG. 32. Referring to FIG. 33, insertion rod 500 can comprise a generally cylindrical body 502 having an introduction end 504 configured to have a pointed or otherwise sharpened tip 506. Cylindrical body 502 preferably comprises a molded, polymeric article. In some embodiments, cylindrical body 502 can be formed with solid biodegradable polymers such as PLGA, PLA, PCL, PGA, POE, PLGA-PEG block copolymers, PLA-PEG block copolymers, PLC-PEG block copolymers, POE-PEG block copolymers, polydioxanone, ethyl cellulose, hydroxyethyl cellulose, polyarylates, polyanhydrides, polybutyrate and similar with treatment drugs. In some embodiments, anti-fibrotic and/or therapeutic agents can be utilized in conjunction with the treatment drugs and otherwise incorporated into the polymer matrix. The percent of drug incorporated can be range from 1% to 50% preferably from 5% to 30%. In some embodiments, cylindrical body 502 can comprise a porous structure for retaining one or more therapeutic agents in the form of drug particles 508 including treatment drugs as shown in FIG. 34. Alternatively, cylindrical body 502 can comprise an inner body member 510 and exterior coating 512 of treatment drugs as shown in FIG. 35. In some embodiments, inner body member 510 can comprise a solid polymeric structure with exterior coating 512 including the one or more treatment drugs. Alternatively, inner body member 510 can include one or more treatment drugs with exterior coating 512 comprising a polymer barrier membrane for controlling the release rate of the one or more treatment drugs.

Generally, catheter 322 is slidably advanced into the uterine cavity 112 as previously described. Inflation balloon 320 is then inflated into inflated disposition 328 such that the inflation balloon is in contact with the endometrium 118. Insertion rod 500 can then be positioned with tip 506 proximate vaginal wall 111 or endometrium 118 such that a pushing or penetrating instrument can deliver the introduction end 504 through the vaginal wall 111 or endometrium 118 as shown in FIG. 32. With insertion rod 500 positioned within the uterine wall 114, the one or more treatment drugs as well as any additional anti-fibrotic or other therapeutic agents can be absorbed into the vasculature network 124 for delivery to uterine fibroid 120. In addition, the pressure applied against endometrium 118 by the inflation balloon 120 can cause the vascular network 124 to be at least partially occluded or otherwise restricted so as to induce hypoxic/ischemic conditions within uterine fibroid 120.

As discussed previously, various embodiments of the physical device can be utilized in treating male pelvic proliferative conditions such as, for example, the presence of proliferative cells in the prostate or testes. In treating male patients, the proliferative cells can be accessed transperineally for local delivery of one or more anti-proliferative agents for the treatment of male proliferative conditions. The minimally invasive device can comprise a physical structure impregnated with, molded with, coated with or otherwise retaining the one or more treatment drugs. The minimally invasive device generally comprises a physical device capable of maintaining its position proximate tissue to be treated. The physical device can take the form of previously described devices or alternatively, meshes and slings as taught by U.S. Patent Publication Nos. 2002/0161382A1 and 2004/0039453A1 as well as U.S. Pat. No. 6,911,003, all of which are commonly assigned to the assignee of the present application, American Medical Systems of Minnetonka, Minn., and all of which are herein incorporated by reference in their entirety.

Figure 36:
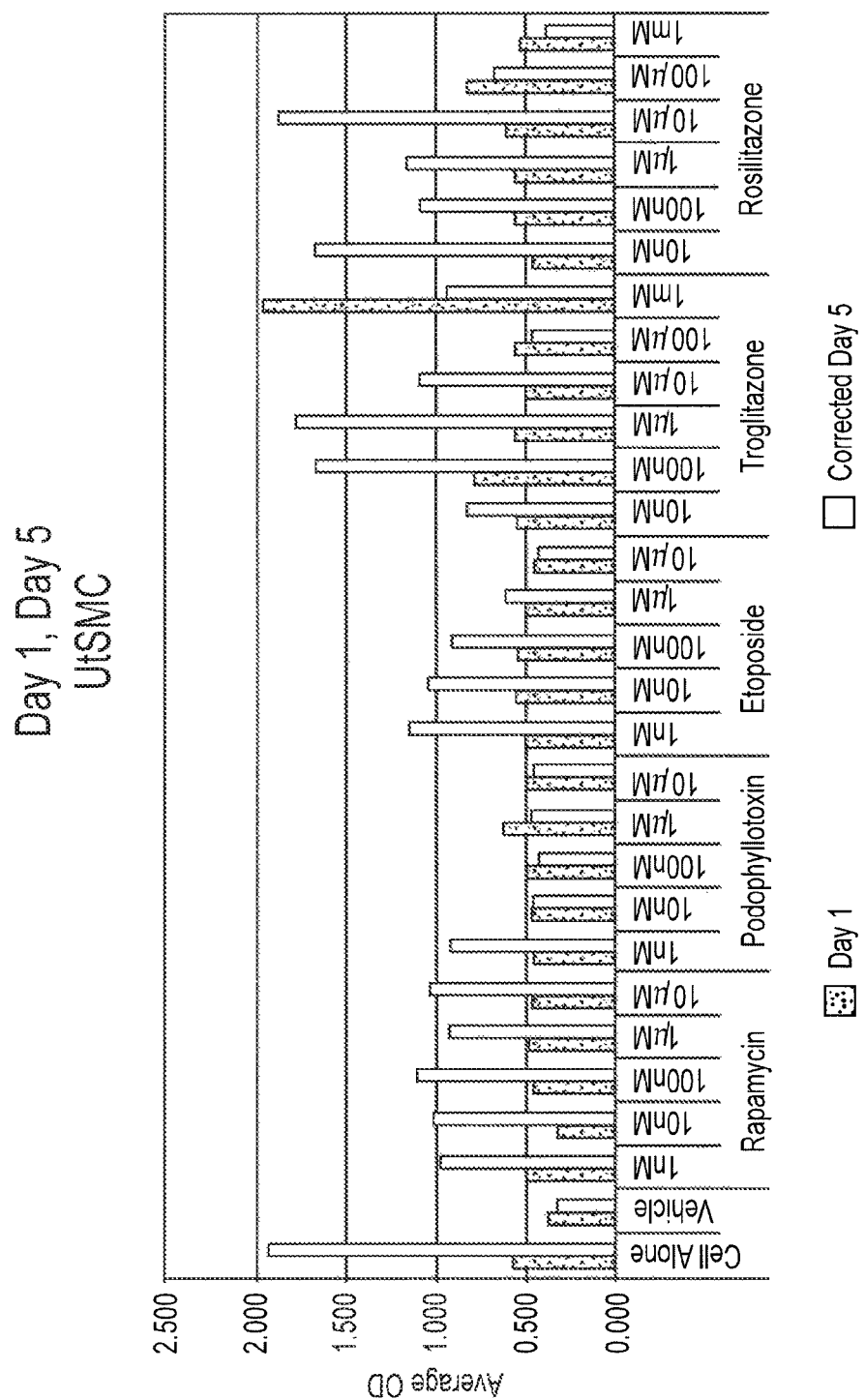
FIG. 36 is a chart illustrating fibroid drug screening results for uterine smooth muscle cells (UtSMC) with Rapamycin, Podophyllotoxin, Etoposide, Troglitazone and Rosilitazone at various concentration levels.
Figure 37:
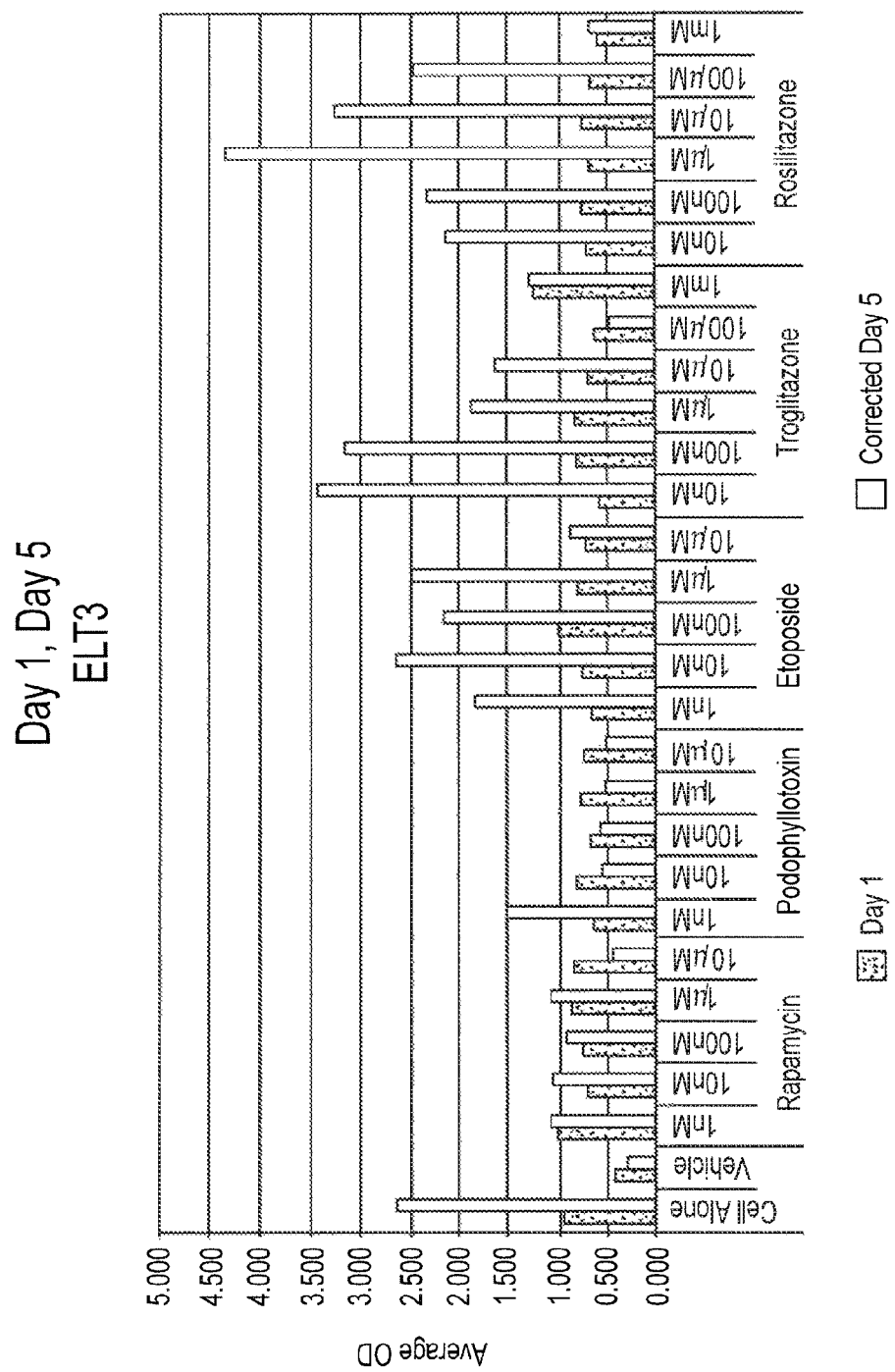
FIG. 37 is a chart illustrating fibroid drug screening results for Eker rat leiomyoma (ELT3) cell line cells with Rapamycin, Podophyllotoxin, Etoposide, Troglitazone and Rosilitazone at various concentration levels.
Figure 38:
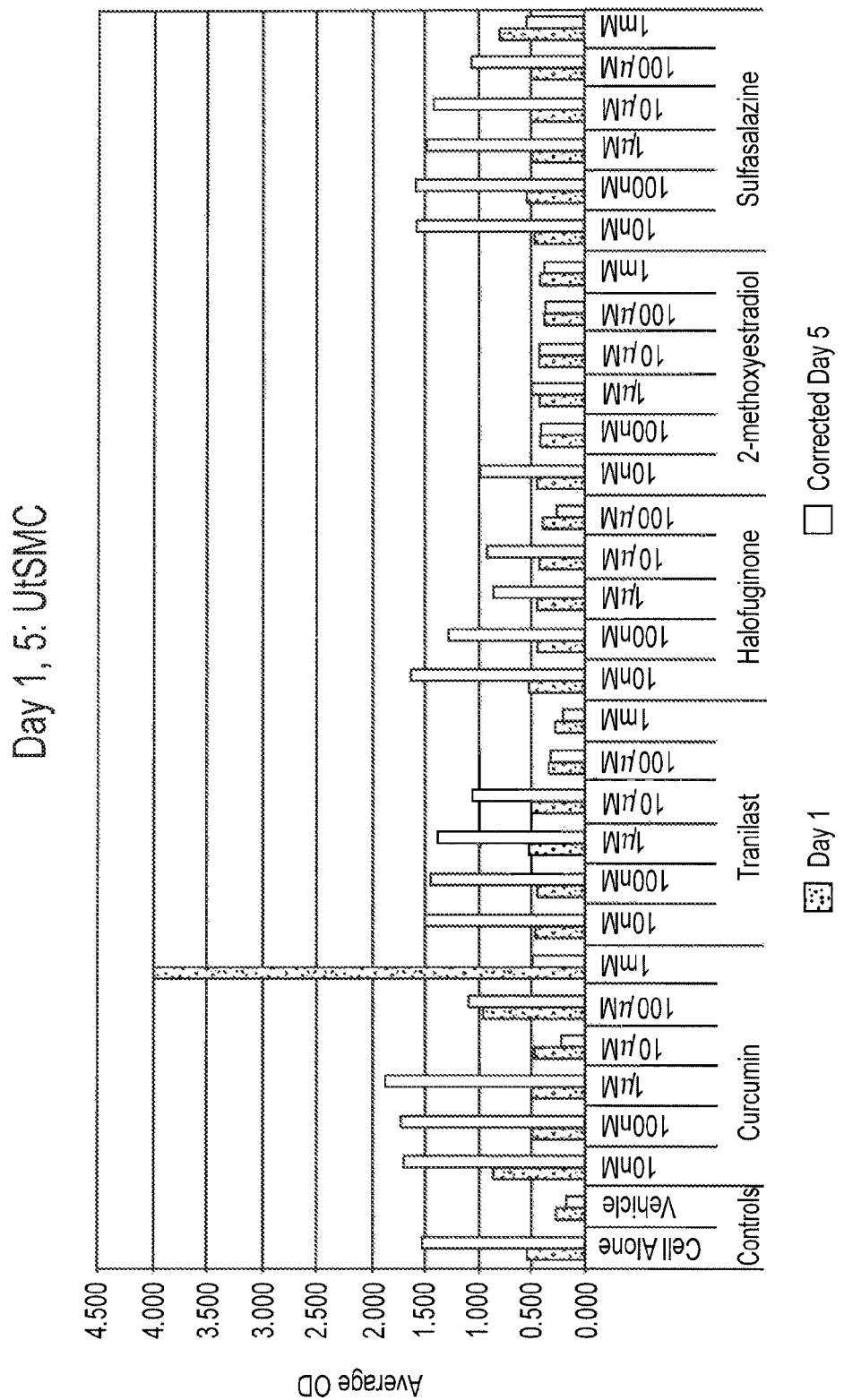
FIG. 38 is a chart illustrating fibroid drug screening results for uterine smooth muscle cells (UtSMC) with Curcumin, Tranilast, Halofuginone, 2-methoxyestradiol and Sulfasalazine at 25 various concentration levels.
Figure 30:
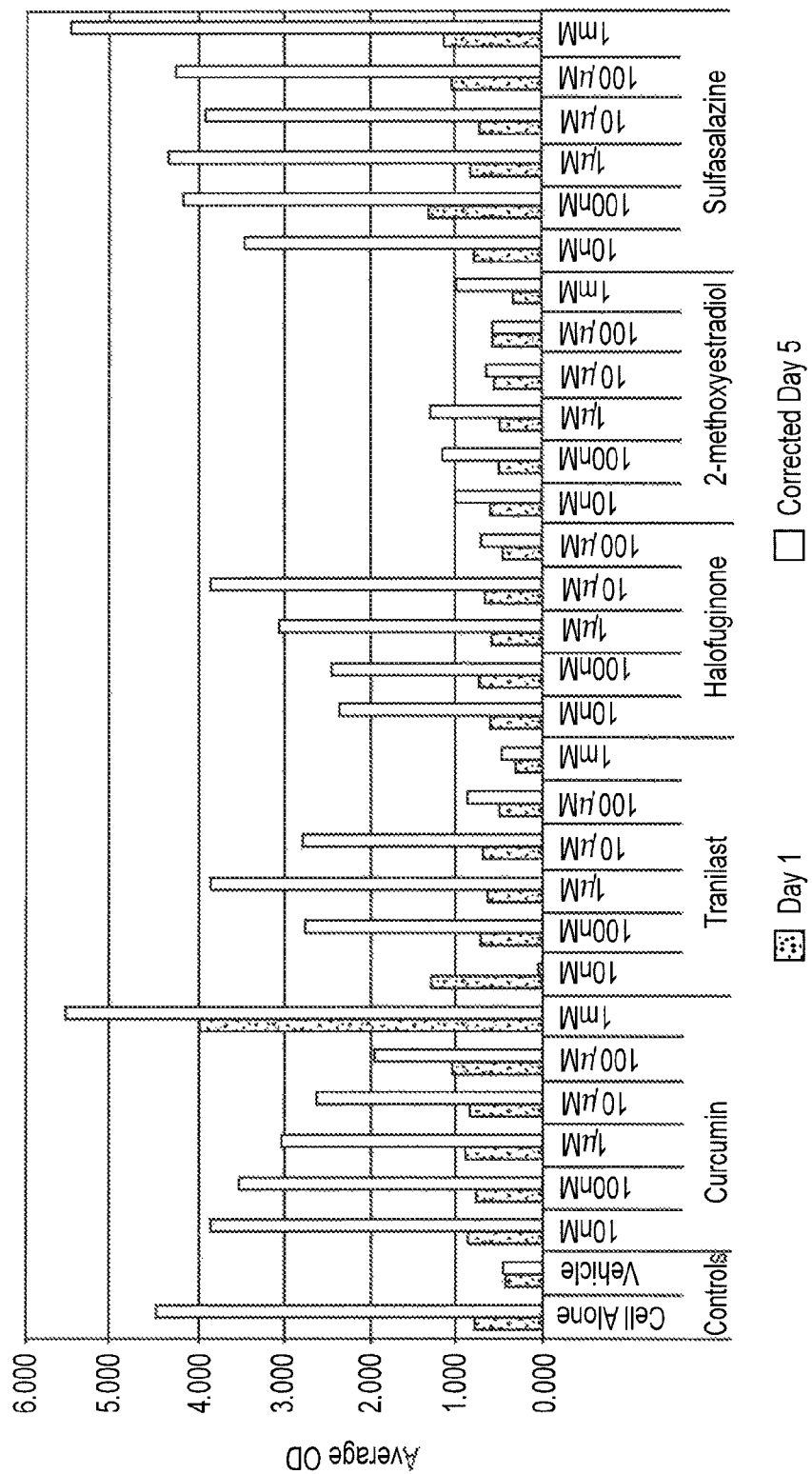
Figure 40:
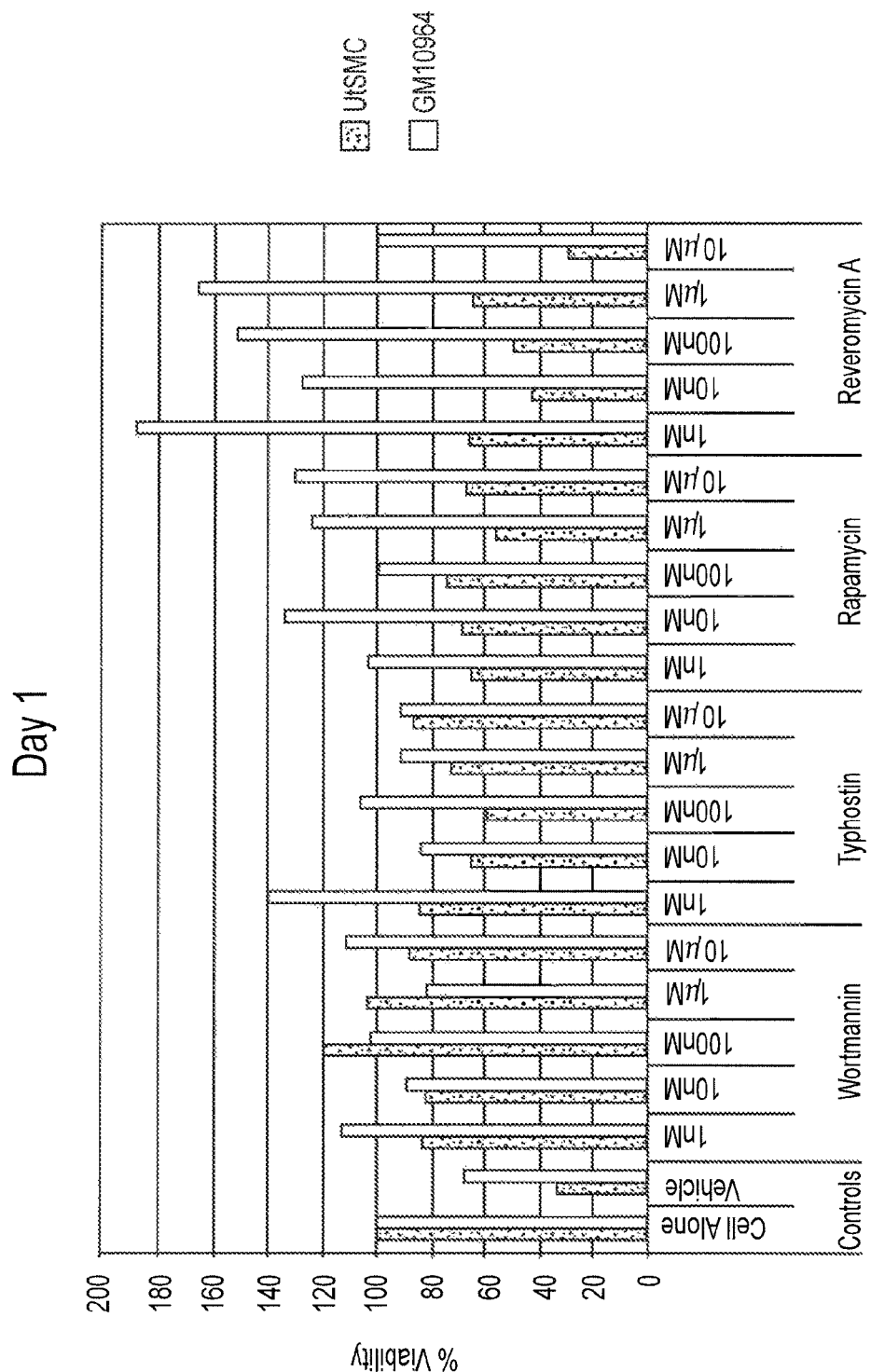
FIG. 40 is a chart illustrating Day 1 cellular viability results for uterine smooth muscle 30 cells (UtSMC) and human leiomyoma (GMI096) cell line cells treated with Wortmannin, Tyrphostin, Rapamycin and Reveromycin A.
Figure 41:
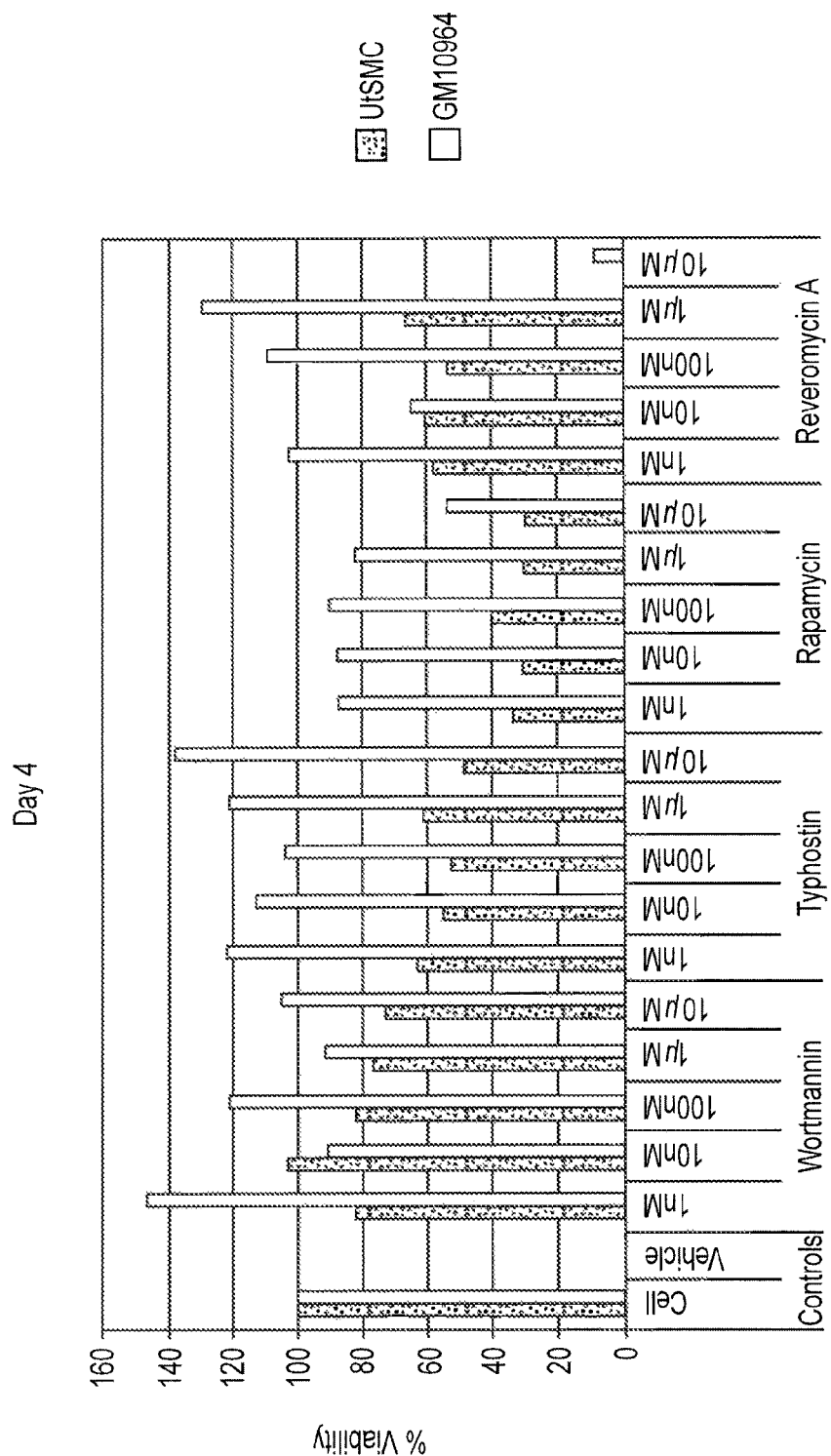
FIG. 41 is a chart illustrating Day 4 cellular viability results for uterine smooth muscle cells (UtSMC) and human leiomyoma (GMI096) cell line cells treated with Wortmannin, Tyrphostin, Rapamycin and Reveromycin A.
Figure 42:
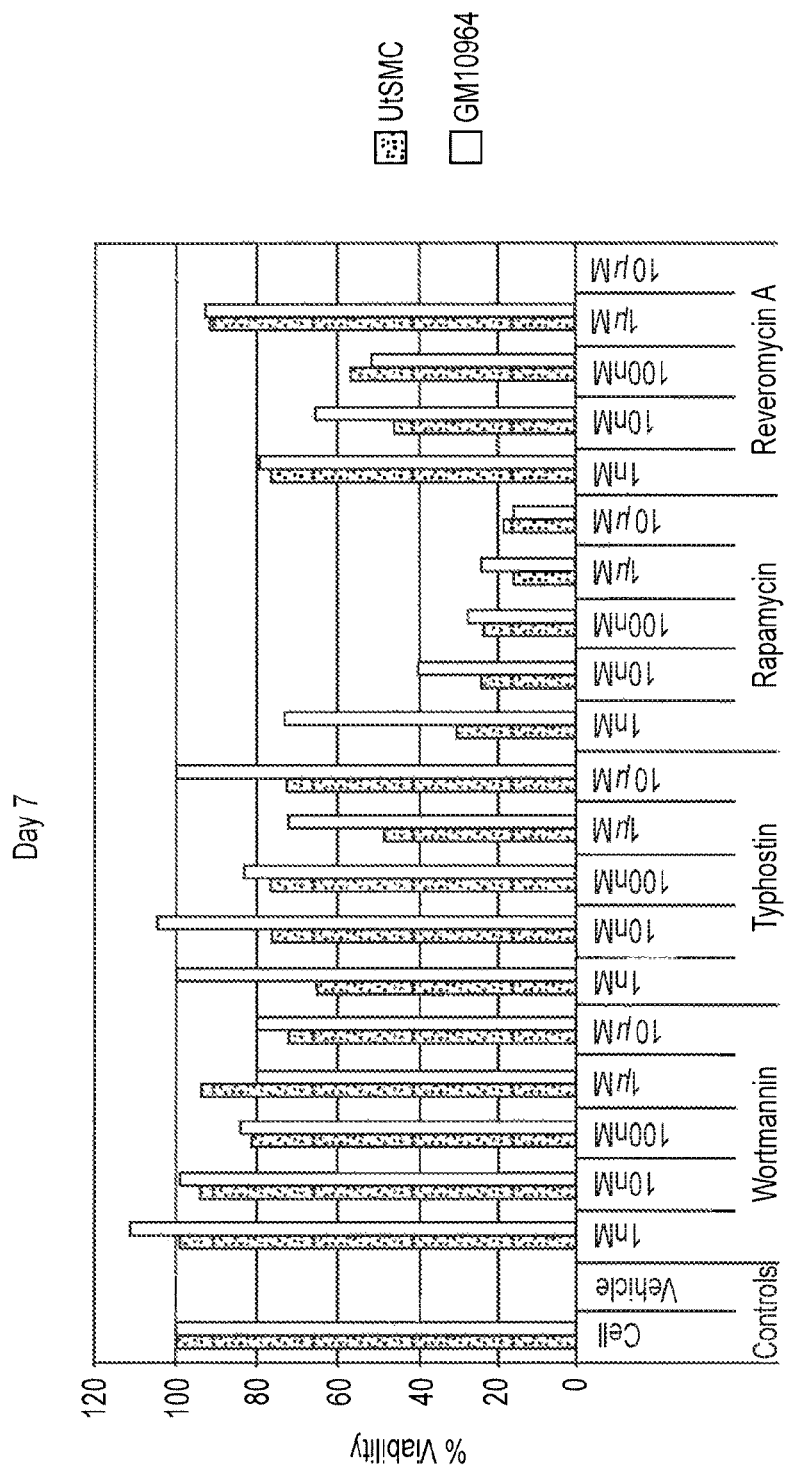
FIG. 42 is a chart illustrating Day 7 cellular viability results for uterine smooth muscle cells (UtSMC) and human leiomyoma (OMI096) cell line cells treated with Wortmannin, Tyrphostin, Rapamycin and Reveromycin A.
Figure 43:
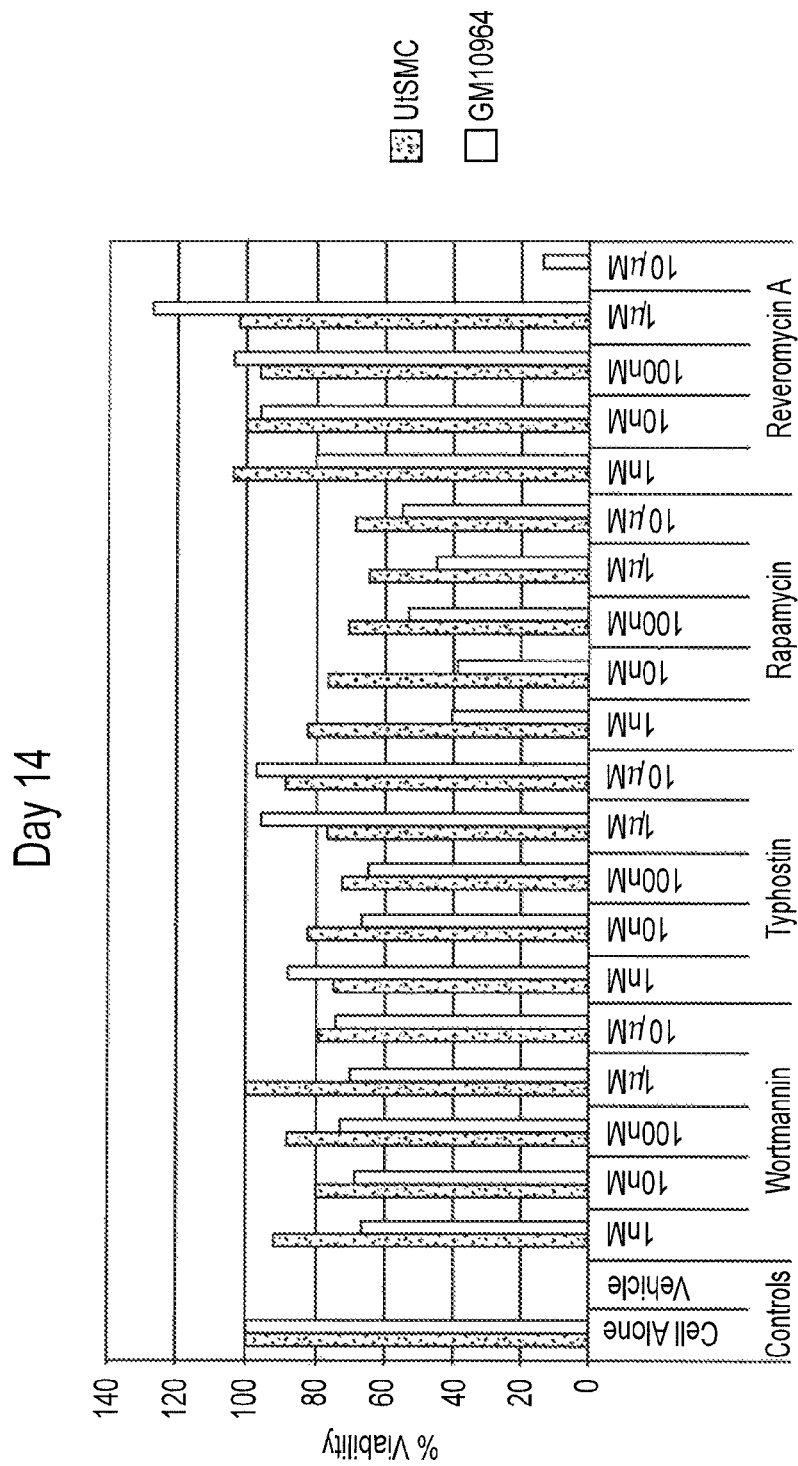
FIG. 43 is a chart illustrating Day 14 cellular viability results for uterine smooth muscle cells (UtSMC) and human leiomyoma (GMI096) cell line cells treated with Wortmannin, Tyrphostin, Rapamycin and Reveromycin A.
Figure 44:
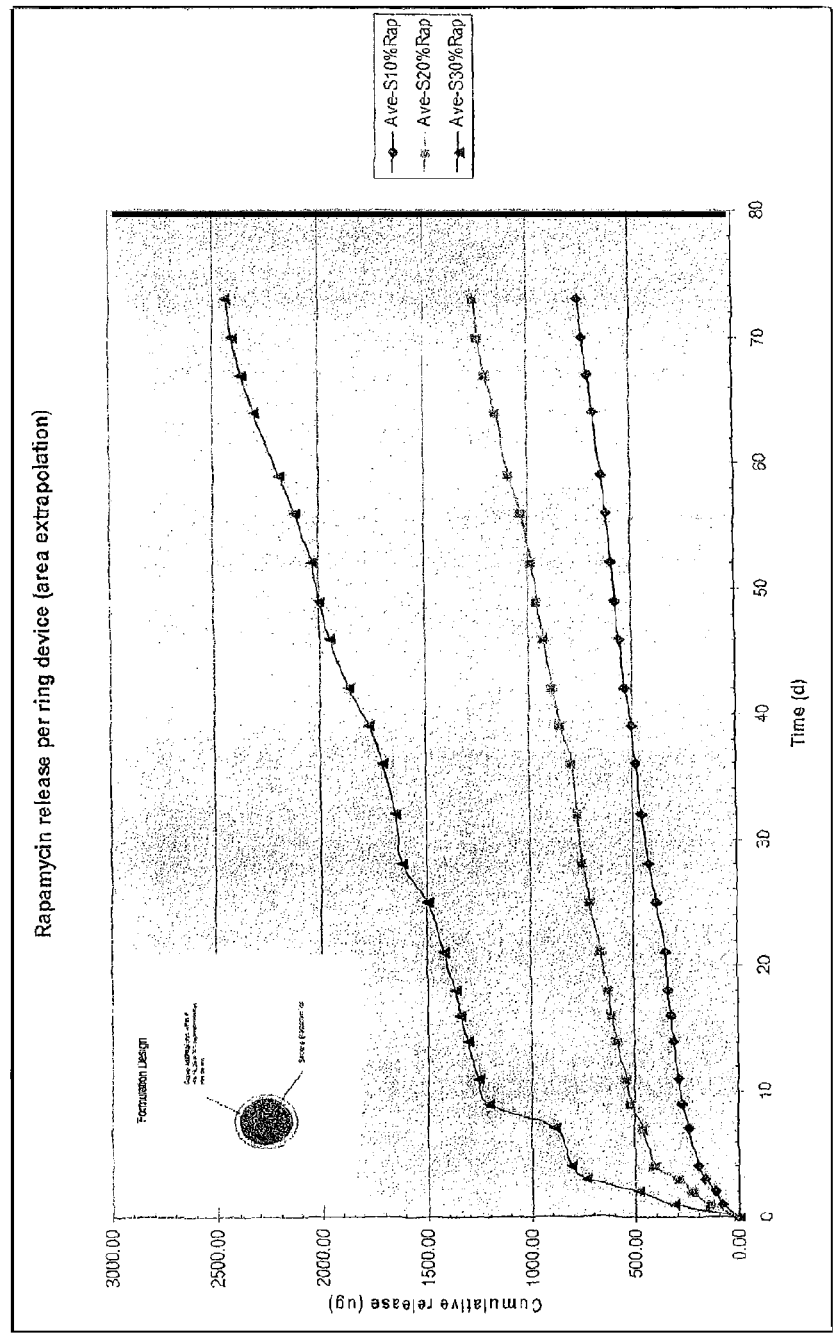
FIG. 44 is a graph illustrating Rapamycin release data for an embodiment of a Drug Eluting Intravaginal Ring.
Figure 45:
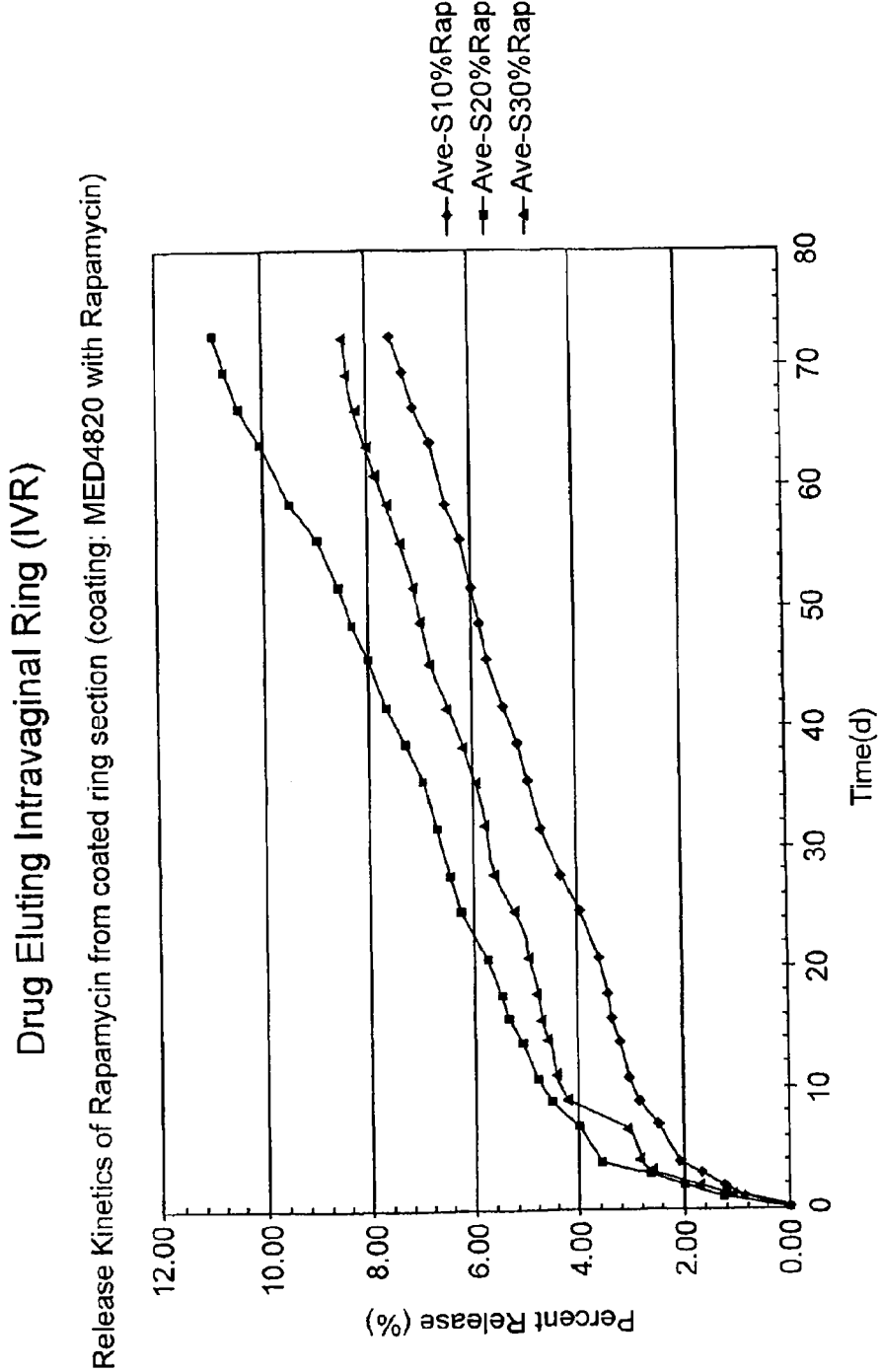
FIG. 45 is a graph illustrating Rapamycin release kinetics for an embodiment of a Drug 10 Eluting Intravaginal Ring.
Figure 46:
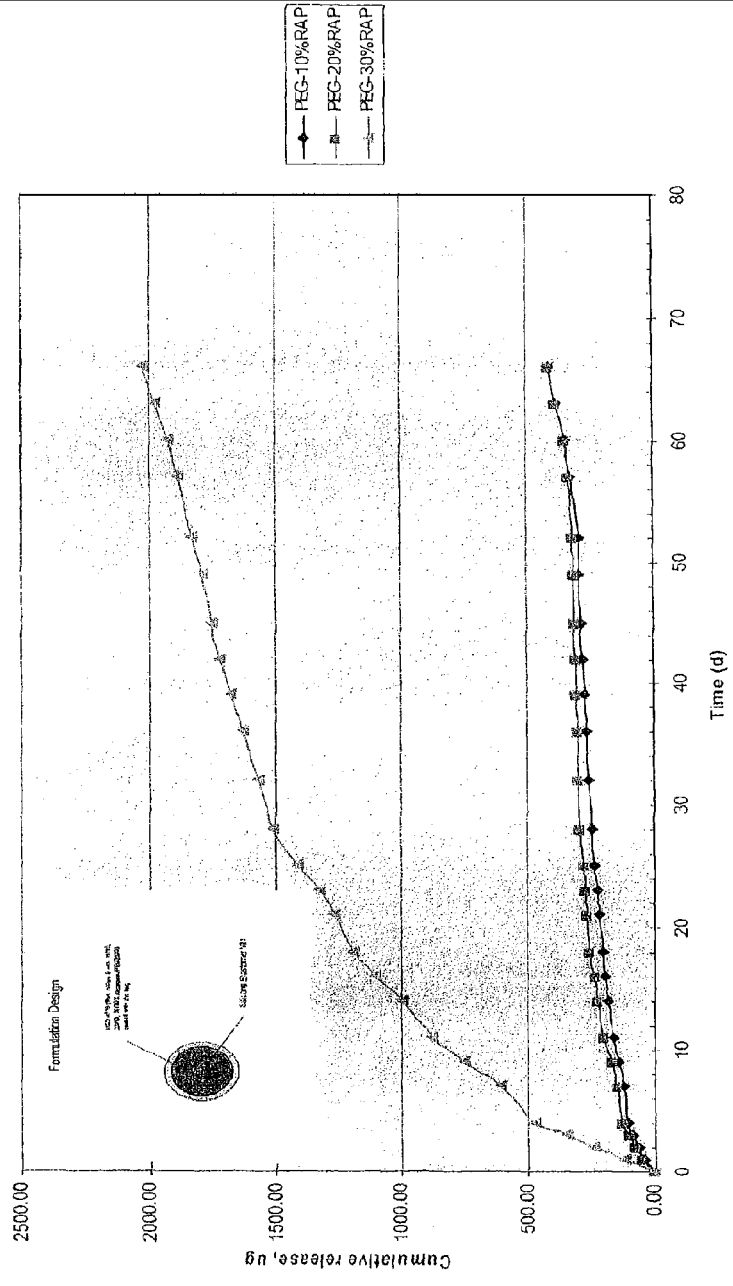
FIG. 46 is a graph illustrating Rapamycin release data for an embodiment of a Drug Eluting Intravaginal Ring.
Figure 47:
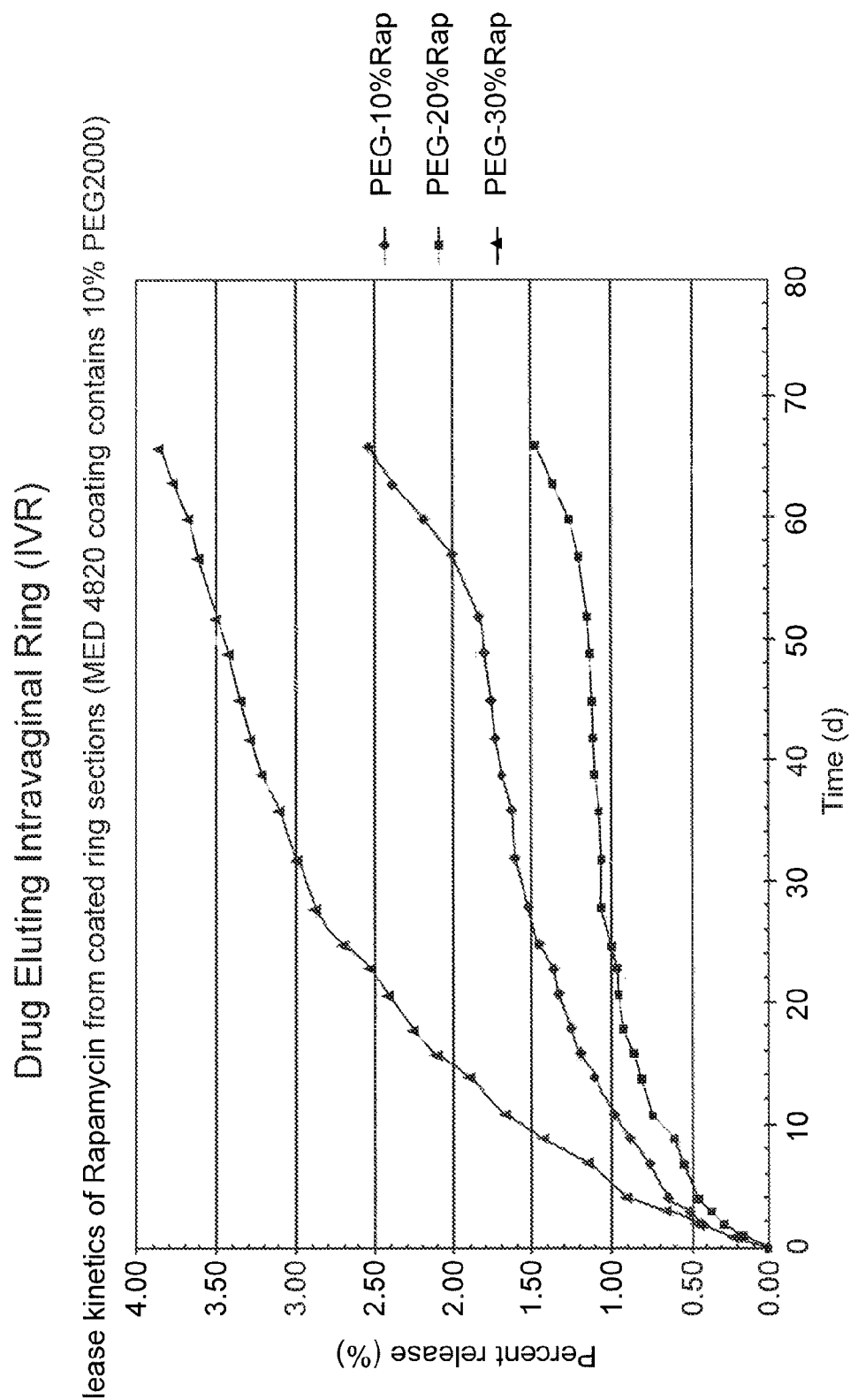
FIG. 47 is a graph illustrating Rapamycin release kinetics for an embodiment of a Drug Eluting Intravaginal Ring.

Referring now to FIGS. 36, 37, 38 and 39, laboratory drug screening results for treatment of uterine smooth muscle cells (UtSMC) and Eker rat leiomyoma (ELT3) cell line cells are illustrated. Referring to FIGS. 36 and 37, Day 1 and Day 5 testing results are displayed for Rapamycin, Podophyllotoxin, Etoposide, Troglitazone and Rosilitazone at various concentration levels. FIGS. 38 and 39 similarly display Day 1 and Day 5 testing results for Curcumin, Tranilast, Halofuginone, 2-methoxyestradiol and Sulfasalazine at various concentrations. In FIGS. 39-39 the effect of the various therapeutic agents on the Average OD of the cells is compared to growth of the cells alone absent the administration of the therapeutic agent.

In FIGS. 40, 41, 42 and 43, laboratory cell viability testing results for uterine smooth muscle cells (UtSMC) and Eker rat leiomyoma (ELT3) cell line cells are illustrated. The charts illustrate percent viability at Day 1 (FIG. 40), Day 4 (FIG. 41), Day 7 (FIG. 42) and Day 14 (FIG. 43) at various administration levels of Wortmannin, Tyrphostin, Rapamycin and Reveromycin A in comparison to control cells absent the administration of the therapeutic agent.

In FIGS. 44, 45, 46 and 47, drug release properties for a drug eluting intravaginal ring are illustrated. The intravaginal ring can comprise a design similar to that previously disclosed as ring 302. The data points in FIGS. 44 and 45 correspond with the compositions previously disclosed with Examples 1, 2 and 3 of Table 1 above while the data points in FIGS. 46 and 47 correspond with the compositions previously disclosed with Examples 4, 5 and 6 of Table 1.

Figure 48:
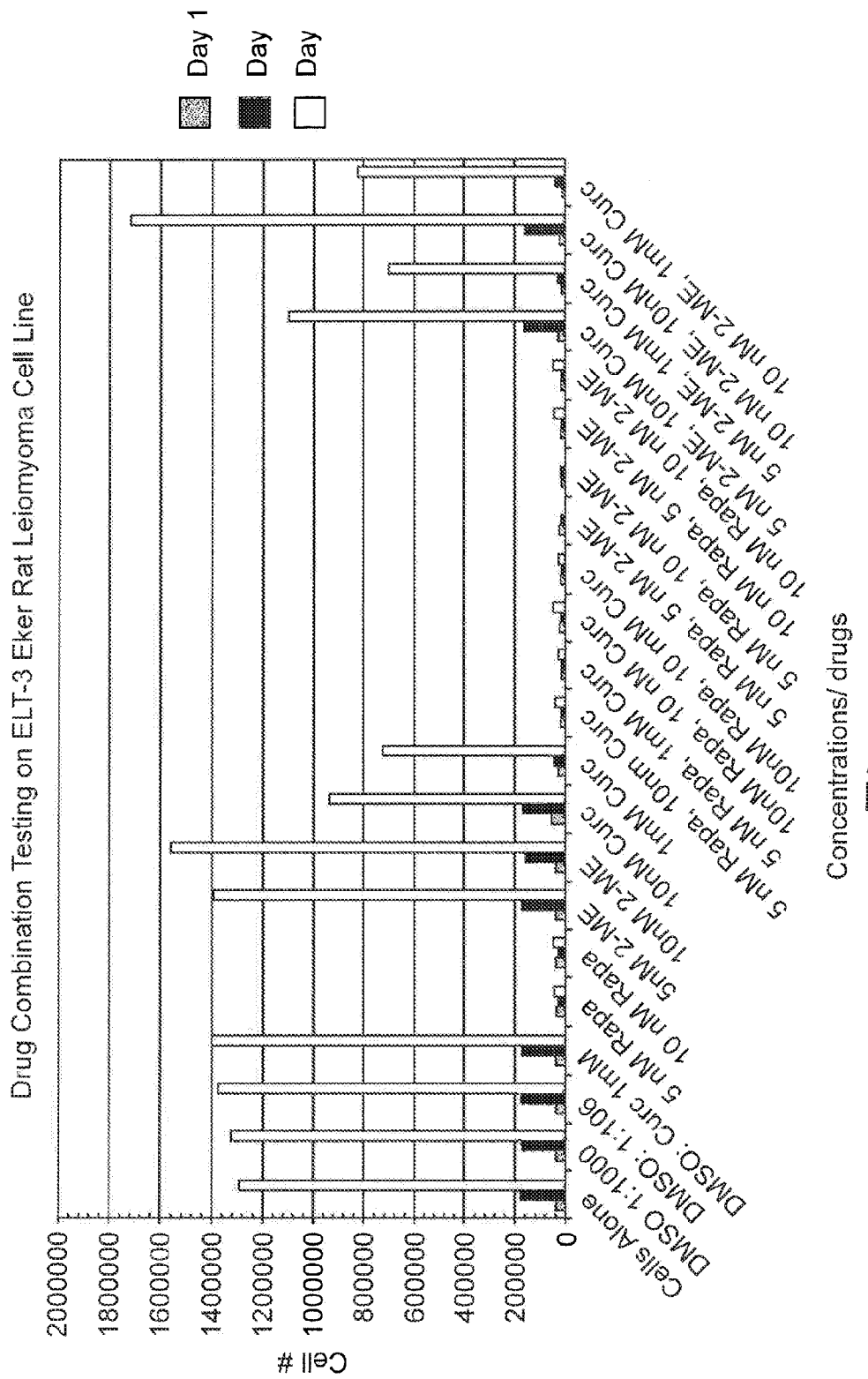
FIG. 48 is a chart illustrating synergistic effects of combinations of two anti-proliferative agents at lower concentration levels than the normal effective doses for the Eker rat leiomyoma (ELT3) cell line cells.
Figure 49:
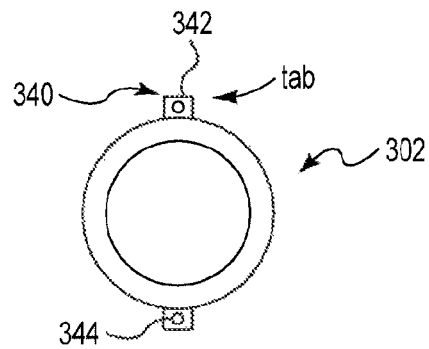
FIG. 49 is a side view of a drug eluting intravaginal ring having tabs according to an embodiment of the present invention.
Figures 50, 51, 52, 53, 54:
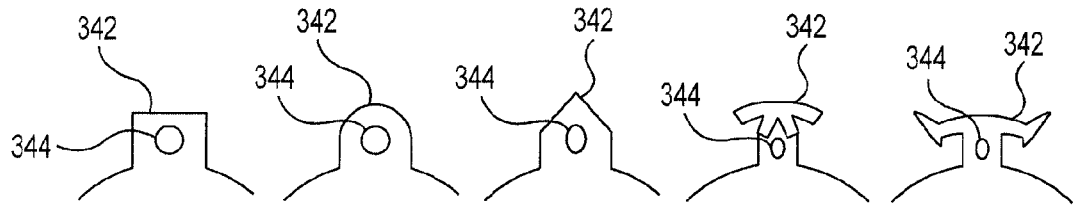
FIG. 50 is a side view of a tab for a drug eluting intravaginal ring according to an embodiment of the present invention.
FIG. 51 is a side view of a tab for a drug eluting intravaginal ring according to an embodiment of the present invention.
FIG. 52 is a side view of a tab for a drug eluting intravaginal ring according to an embodiment of the present invention.
FIG. 53 is a side view of a tab for a drug eluting intravaginal ring according to an embodiment of the present invention.
FIG. 54 is a side view of a tab for a drug eluting intravaginal ring according to an embodiment of the present invention.
Figure 55:
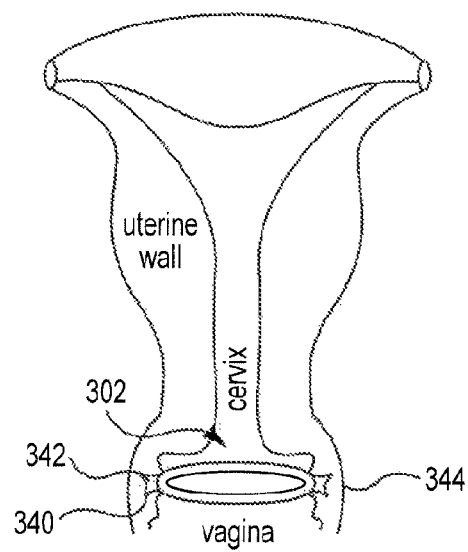
FIG. 55 is a representative view of the drug eluting intravaginal ring depicted in FIG. 49 positioned within an intravaginal cavity.

FIG. 48 illustrates the synergistic effect of treatment drugs comprising a combination of two anti-proliferative agents at lower concentration levels than the normal effective doses for the ELT-3 cell line. By providing for lower concentration levels of anti-proliferative agents, the combinations minimize the adverse or toxic effects resulting from higher concentrations of anti-proliferative agents associated with individual use of a single anti-proliferative agent, or through a systemic delivery of the anti-proliferative agents as opposed to localized delivery.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

The invention claimed is:

1. A vaginally introduced implant configured for use in a woman and for treating pathologic proliferative conditions of uterine tissue comprising:
a drug-eluting treatment element comprising at least one pathologic proliferative condition treatment drug, the treatment element positionable proximate to a location of uterine proliferative cells, wherein the drug-eluting treatment element is adapted to elute the treatment drug over an effective treatment period; and
a retention element operably linked to the treatment element and positionable within a body cavity to maintain the treatment element proximate to the location of uterine proliferative cells.

2. The vaginally introduced implant of claim 1, wherein the retention element further comprises a body sized to engage at least two tissue walls of a body lumen proximate the uterine proliferative cells to maintain the treatment element proximate to the location of the uterine proliferative cells.

3. The vaginally introduced implant of claim 1, wherein the retention element further comprises a biological adhesive for adhering the retention element to a wall of a body lumen so as to maintain the treatment element proximate to the location of the uterine proliferative cells.

4. The vaginally introduced implant of claim 3, wherein the biological adhesive is biodegradable, wherein the biological adhesive is adapted to degrade over the effective treatment period to release the vaginally introduced implant at the end of the effective treatment period.

5. The vaginally introduced implant of claim 1, wherein the retention element further comprises:
a plurality of approximating elements extendable from the retention element for engaging a tissue wall proximate the uterine proliferative cells;
wherein the approximating elements are adjustable between a retracted position preventing the approximating elements from catching on tissue while positioning the treatment element and an extended position for engaging the tissue wall proximate the uterine proliferative cells.

6. The vaginally introduced implant of claim 1 wherein implant comprises a coating and the treatment drug is present in the coating.

7. The vaginally introduced implant of claim 6 wherein the treatment drug is coated over the entire implant.

8. The vaginally introduced implant claim 1, wherein the at least one treatment drug is selected from a group consisting of anti-proliferative agents, angiogenesis inhibitors or combinations thereof.

9. The vaginally introduced implant of claim 8 wherein the treatment drug comprises an anti-proliferative agent.

10. The vaginally introduced implant of claim 9 wherein the anti-proliferative agent is selected from the group consisting of rapamycin, podophyllotoxin, etoposide, troglitazone rosilitazone, curcumin, halofuginone, and 2-methoxyestradiol.

11. The vaginally introduced implant of claim 9 further comprising an angiogenesis inhibitor.

12. The vaginally introduced implant of claim 1, wherein the retention element further comprises:
an anchor having:

at least one retractable anchor arm positionable within a fallopian tube to maintain the treatment element proximate to the uterine proliferative cells and block the fallopian tube;

wherein the treatment element comprises a stem operably linked to the at least one anchor arm;

wherein the anchor arm is adjustable between a retracted position preventing the anchor arm from catching on tissue while positioning the treatment element proximate to the location of uterine proliferative cells and a extended position for anchoring the treatment element proximate to the location of uterine proliferative cells.

13. The vaginally introduced implant of claim 12 wherein the at least one anchor arm further comprises a spring for biasing the anchor arm to the extended position.

14. The vaginally introduced implant of claim 12, wherein the retractable arm comprises nickel titanium metal such that the retractable arm is movable between the extended and retracted position by applying different temperatures to the retractable arm.

15. The vaginally introduced implant of claim 12 wherein the stem comprises a coating and the treatment drug is present in the coating.

16. The vaginally introduced implant of claim 12, further comprising a ring operably linked to the stem and positionable within the vaginal cavity and adapted to elute the at least one treatment drag into the vaginal cavity over the effective treatment period.

17. The implant of claim 16, wherein at least a portion of the ring comprises a biodegradable material, wherein the biodegradable portion of the ring degrades gradually after the ring is positioned within the vaginal cavity to gradually administer the at least one treatment drug over the effective treatment period.

* * * * *

UNITED STATES PATENT AND TRADEMARK OFFICE
CERTIFICATE OF CORRECTION

| | | |
|---|---|---|
| PATENT NO. | : 8,597,262 B2 | Page 1 of 2 |
| APPLICATION NO. | : 13/383147 | |
| DATED | : December 3, 2013 | |
| INVENTOR(S) | : Canifax et al. | |

It is certified that error appears in the above-identified patent and that said Letters Patent is hereby corrected as shown below:

On the Title Page, in item (75), under "Inventors", in Column 1, Line 3, delete "Edouard" and insert -- Édouard --, therefor.

Title Page 2, in item (56), under "OTHER PUBLICATIONS", in Column 2, Line 4, delete "Laparascopists," and insert -- Laparoscopists, --, therefor.

Title Page 2, in item (56), under "OTHER PUBLICATIONS", in Column 2, Lines 14-15, delete "Hemmorhage, """ and insert -- Hemorrhage," --, therefor.

In the Specification

In Column 1, Lines 14-22, delete "PRIORITY CLAIM
The present application claims priority to U.S. Provisional Application Ser. Nos. 61/244,385, filed Jul. 9, 2009 and entitled "INTRAVAGINAL TREATMENT OF UTERINE FIBROIDS", and 61/238,943, filed Sep. 1, 2009 and entitled "INTRAVAGINAL TREATMENT OF UTERINE FIBROIDS," each of which are herein incorporated by reference in their entirety.".

In Column 1, Line 36, delete "are the" and insert -- is the --, therefor.

In Column 4, Line 51, delete "drugst." and insert -- drugs. --, therefor.

In Column 5, Line 33, delete "is as" and insert -- is a --, therefor.

In Column 5, Line 59, delete "CELT3)" and insert -- (ELT3) --, therefor; and Column 5, Line 67, delete "CELT3)" and insert -- (ELT3) --, therefor.

Signed and Sealed this
Twenty-sixth Day of May, 2015

Michelle K. Lee
*Director of the United States Patent and Trademark Office*

CERTIFICATE OF CORRECTION (continued)
U.S. Pat. No. 8,597,262 B2

In Column 6, Line 6, delete "CELT3)" and insert -- (ELT3) --, therefor; Column 6, Line 12, delete "CELT3)" and insert -- (ELT3) --, therefor; and Column 6, Line 19, delete "CELT3)" and insert -- (ELT3) --, therefor.

In Column 9, Lines 13-38, delete "is generally.......myometrium 116." and insert the same at Line 12, after "uterus 102", as a continuation paragraph.

In Column 10, Line 9, delete "Betulinic acid" and insert -- betulinic acid --, therefor; and Column 10, Line 10, delete "busultan, busultan," and insert -- busulfan, --, therefor.

In Column 13, Line 2, delete "treatment drugs 260" and insert -- treatment drugs --, therefor.

In Column 19, Line 67, delete "vaginal wall I11," and insert -- vaginal wall 111, --, therefor.

In Column 20, Line 8, delete "nanopsheres" and insert -- nanospheres --, therefor.

In the Claims

In Column 22, Line 52, in Claim 8, delete "implant claim" and insert -- implant of claim --, therefor.

In Column 24, Line 9, in Claim 16, delete "drag" and insert -- drug --, therefor; and Column 24, Line 11, in Claim 17, delete "implant of claim" and insert -- vaginally introduced implant of claim --, therefor.